United States Patent
Honda

(10) Patent No.: US 11,185,029 B2
(45) Date of Patent: Nov. 30, 2021

(54) METHOD FOR PRODUCING PLANT BODY

(71) Applicant: KUBOTA CORPORATION, Osaka (JP)

(72) Inventor: Mitsuru Honda, Osaka (JP)

(73) Assignee: Kubota Corporation, Osaka (JP)

( * ) Notice: Subject to any disclaimer, the term of this patent is extended or adjusted under 35 U.S.C. 154(b) by 0 days.

(21) Appl. No.: 16/637,109

(22) PCT Filed: Aug. 2, 2018

(86) PCT No.: PCT/JP2018/028999
§ 371 (c)(1),
(2) Date: Feb. 6, 2020

(87) PCT Pub. No.: WO2019/031376
PCT Pub. Date: Feb. 14, 2019

(65) Prior Publication Data
US 2020/0245578 A1    Aug. 6, 2020

(30) Foreign Application Priority Data

Aug. 7, 2017 (JP) .............................. JP2017-152348

(51) Int. Cl.
*A01H 4/00* (2006.01)
*A01H 5/02* (2018.01)
*C12N 5/04* (2006.01)

(52) U.S. Cl.
CPC ................ *A01H 4/00* (2013.01); *A01H 5/02* (2013.01); *C12N 5/04* (2013.01)

(58) Field of Classification Search
CPC ........... B01L 3/0268; B01L 2300/0819; C12N 5/0677; C12N 5/0062; C12N 5/0671; B33Y 70/00; G01N 2035/00168

USPC ......... 101/483; 435/4, 29, 1.1, 410; 347/146
See application file for complete search history.

(56) References Cited

U.S. PATENT DOCUMENTS

2017/0073634 A1    3/2017  Okada et al.

FOREIGN PATENT DOCUMENTS

| JP | 2005-130759 A | 5/2005 |
| JP | 2009-207963 A | 9/2009 |
| JP | 2016-111988 A | 6/2016 |
| JP | 2017-55670 A | 3/2017 |
| WO | WO-2009/137135 A2 | 11/2009 |
| WO | 2016/092106 A1 | 6/2016 |

OTHER PUBLICATIONS

Wicaksono et al. 2015. J. Plant Develop. 22:135-141.*
Arai et al. 2011. Biofabrication 3:1-7, 2011.*
Wicaksono et al., "Plant Bioprinting: Novel Perspective for Plant Biotechnology," J. Plant Develop. 22 (2015), pp. 135-141.
International Search Report dated Nov. 6, 2018 in corresponding International Patent Application No. PCT/JP2018/028999.
International Preliminary Report on Patentability dated Feb. 20, 2020 in corresponding International Patent Application No. PCT/JP2018/028999.
European Search Report dated Jun. 30, 2020 in corresponding European Patent Application No. 18844781.7. 7 pages.

* cited by examiner

*Primary Examiner* — Keith O. Robinson
(74) *Attorney, Agent, or Firm* — McCarter & English, LLP; David G. Conlin

(57) ABSTRACT

An aspect of the present invention provides a method of forming a plant body having a desired three dimensional shape. A method of producing a plant body in accordance with an embodiment of the present invention includes the step of forming a three-dimensional body which contains plant cells having differentiation ability.

11 Claims, 10 Drawing Sheets

PLANT GROWTH DIRECTION

METHOD FOR PRODUCING PLANT BODY

TECHNICAL FIELD

The present invention relates to a method of producing a plant body.

BACKGROUND ART

In general, the following method is known as an effective method of growing virus-free seedlings or the like of, for example, strawberry varieties. First, shoot apex cells or the like collected from an excellent individual are cultured in an aseptic condition, so that a mass of undifferentiated cells is formed. The mass of undifferentiated cells is called a callus. Next, a plant hormone, whose concentration has been adjusted to a predetermined concentration, is added to the callus. This produces an adventitious bud or the like. Then, the adventitious bud or the like is used to regenerate a plant body. For example, Patent Literature 1 discloses a technique as described above.

Meanwhile, Patent Literature 2 discloses a method of producing a microbead gel. Patent Literature 2 also discloses that cells can be encapsulated in the microbead gel. Further, Patent Literature 3 discloses a method of culturing cells in three dimensions with use of a three-dimensional cell culture carrier containing a carbon nanomaterial.

CITATION LIST

Patent Literature

[Patent Literature 1]
Japanese Patent Application Publication Tokukai No. 2017-55670 (Publication date: Mar. 23, 2017)
[Patent Literature 2]
Japanese Patent Application Publication Tokukai No. 2009-207963 (Publication date: Sep. 17, 2009)
[Patent Literature 3]
Japanese Patent Application Publication Tokukai No. 2005-130759 (Publication date: May 26, 2005)

SUMMARY OF INVENTION

Technical Problem

However, there has been a room for improvement in the above-described conventional techniques, from the viewpoint of forming a plant body having a desired three-dimensional shape. For example, the technique disclosed in Patent Literature 1 is incapable of controlling the shape of a grown body of a plant and the shape of the grown body of the plant has been left to that plant itself. Further, the techniques disclosed in Patent Literatures 2 and 3 assume use of cells which have already differentiated.

An aspect of the present invention is attained in view of the above problems. An object of the present invention is to provide a method of forming a plant body having a desired three-dimensional shape.

Solution to Problem

In order to solve the above problems, the inventor of the present invention made diligent studies. As a result, the inventor has found that a plant body having a desired three-dimensional shape can be obtained by forming a three-dimensional body with use of plant cells having differentiation ability, and thereby has accomplished the present invention. The present invention includes the following aspects.

<1> A method of producing a plant body, including the step (forming step) of: forming a three-dimensional body which contains plant cells having differentiation ability.

<2> The method as described in <1>, wherein: the plant cells having differentiation ability are dedifferentiated cells obtained from a callus.

<3> The method as described in <1> or <2>, wherein: in the forming step, gel beads containing the plant cells having differentiation ability are arranged in a shape that is identical to a rough shape of a target plant body.

<4> The method as described in <3>, wherein: the three-dimensional body is formed from (a) the gel beads containing the plant cells having differentiation ability and (b) gel beads containing no plant cell having differentiation ability.

<5> The method as described in any one of <1> to <4>, wherein: the plant cells having differentiation ability are plant cells derived from two or more species of plants.

<6> The method as described in any one of <1> to <5>, further including the step (organization-promoting step) of: adding an organization-promoting agent to the plant cells having differentiation ability, the organization-promoting agent containing a component that promotes organization of the plant cells, the organization-promoting step being carried out before, after or simultaneously with the forming step.

<7> The method as described in <6>, wherein: in the organization-promoting step, the organization-promoting agent includes different kinds of organization-promoting agents, and the different kinds of organization promoting agents are added respectively to two or more parts of the three-dimensional body.

<8> The method as described in <6> or <7>, further including the step (culture step) of: culturing the three-dimensional body, after the forming step and the organization-promoting step.

<9> The method as described in <8>, wherein: in the culture step, the three-dimensional body is cultured so as to be joined to another plant body.

<10> The method as described in <8> or <9>, wherein: in the culture method, a length direction of a part of the three-dimensional body which part corresponds to a stem is kept parallel to a gravitational direction.

<11> The method as described in any one of <1> to <10>, wherein: in the forming step, the three-dimensional body is formed by a dipping method, an ink jet method, or a dispenser method.

<12> The method as described in any one of <6> to <10>, wherein: in the organization-promoting step, the organization-promoting agent is added to the three-dimensional body or the plant cells having differentiation ability, by a dipping method, an ink jet method, or a dispenser method.

<13> The method as described in <12>, wherein the organization-promoting agent is added to the three-dimensional body, by a method capable of carrying out gradation control.

<14> The method as described in any one of <1> to <13>, wherein: the three-dimensional body is subjected to arrangement control of at least leaves or stems.

<15> The method as described in any one of <1> to <14>, wherein: the three-dimensional body includes at least one of a hollow part and a groove which are open at a surface of the three-dimensional body.

Advantageous Effects of Invention

An aspect of the present invention advantageously makes it possible to provide a method of forming a plant body having a desired three-dimensional shape.

DESCRIPTION OF EMBODIMENTS

Figure 1:
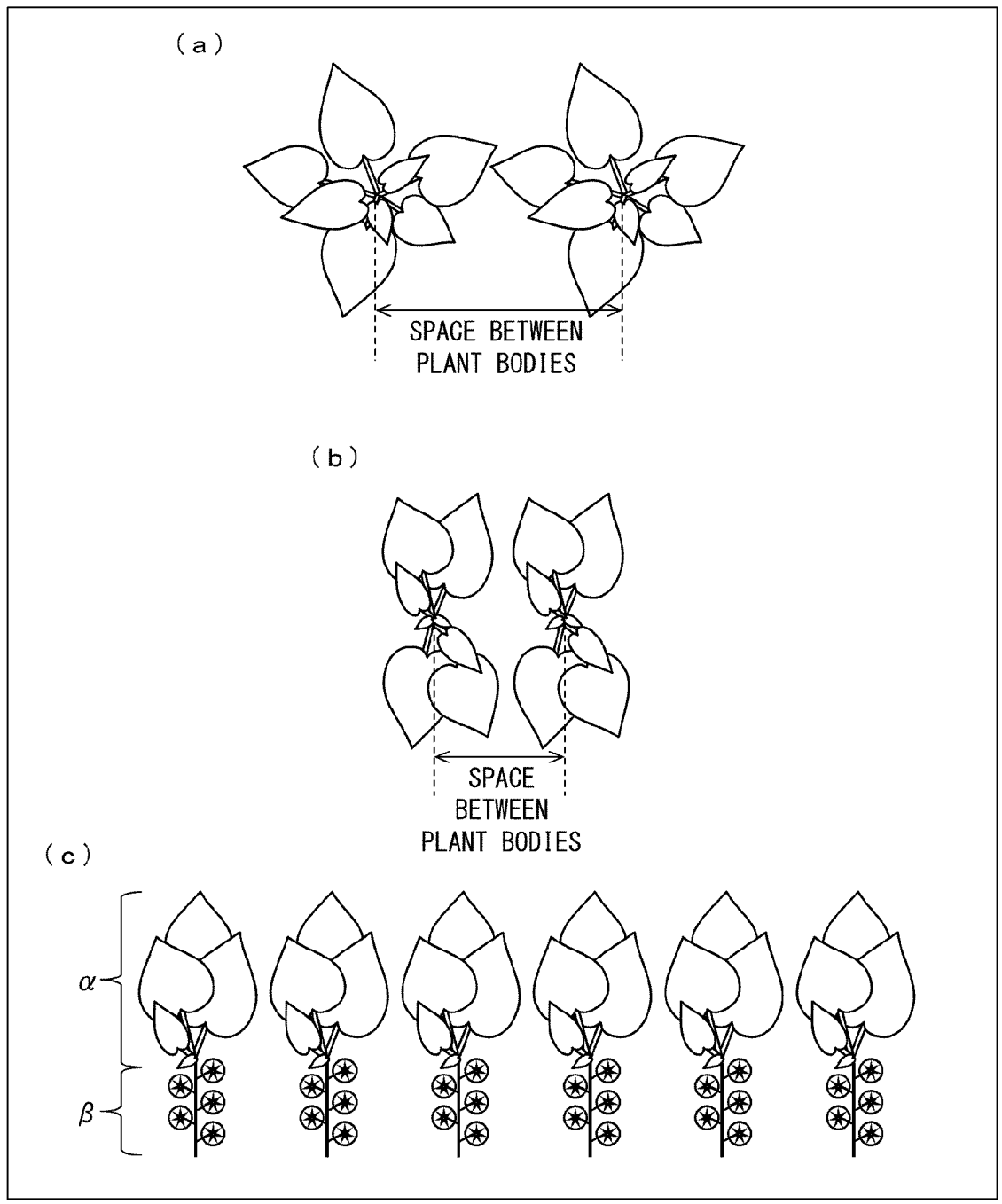
FIG. 1 is a view schematically illustrating a shape of a plant body in accordance with an embodiment of the present invention.

An embodiment of the present invention will be discussed below. Note, however, that the present invention is not limited to such an embodiment. Note that a numerical range "A to B" herein means "not less than A and not more than B" unless otherwise specified in the present specification. For convenience of description, members having identical functions are assigned identical referential numerals, and their descriptions are omitted.

A method of producing a plant body in accordance with an embodiment of the present invention includes the step (forming step) of forming a three-dimensional body which contains plant cells having differentiation ability. According to the method of producing a plant body, a plant body having a desired three-dimensional shape can be obtained since the plant body is obtained from the three-dimensional body which has been formed in the forming step. The details of the above method will be discussed below.

[1. Forming Step]

The forming step is the step of forming a three-dimensional body which contains plant cells having differentiation ability. The forming step allows a plant body to be formed in a desired shape, and also allows the plant cells to differentiate into a desired tissue. This makes it possible to design a plant body with a high degree of freedom.

<1-1. Plant Cells>

In the forming step, at least plant cells having differentiation ability are used. The plant cells having differentiation ability may be, for example, dedifferentiated cells. The dedifferentiated cells may be, for example, cells obtained from a callus which has been obtained from cells collected from a plant tissue. Examples of such a plant tissue encompass roots, stems, leaves, petals, seeds, embryos, ovules, ovaries, anthers, pollens, and growth points (shoot apical meristems and root apical meristems). In particular, cells of shoot apical meristems (shoot apex cells) are preferable since those cells are virus-free.

The callus can be formed by extracting the plant tissue and culturing the plant tissue in a culture medium which contains nutrients. For example, callus induction can be performed by adding, to cells collected from the plant tissue, auxin and cytokinin (which are plant hormones) at substantially the same concentrations. The culture medium can be a liquid medium or any medium which is generally used for plant culture. Examples of such a culture medium encompass an MS medium and an LS medium.

It is preferable that subsequently, (i) cells be isolated from the callus or (ii) the callus be broken up so as to be in the state of a spheroid which is made of a mass of cells, by using an enzyme on the callus which has been formed. In this case, the three-dimensional body can be more easily formed. The enzyme may be cellulase, pectinase, or the like. It is preferable that an aqueous solution of any of these enzymes be brought into contact with the callus.

Note that the three-dimensional body can be formed by directly using cells obtained from a plant tissue other than using the cells which have been obtained through the callus and each of which has differentiation ability. Note, however, that in this case, at least some of the cells having been obtained from the plant tissues need to be dedifferentiated after the three-dimensional body has been formed by using those cells obtained from the plant tissue.

Further, the three-dimensional body can be also formed by using both of plant cells having differentiation ability and plant cells which have differentiated into a specific tissue. The plant cells which have differentiated into a specific tissue mean, for example, (a) plant cells obtained from a plant tissue or (b) plant cells which are obtained as a result of differentiation of plant cells having differentiation ability, by subjecting the plant cells having the differentiation ability to the step of promoting organization (organization-promoting step).

The plant cells can be plant cells from any of seed plants, pteridophytes and bryophytes. The seed plants can be angiosperms or gymnosperms. The angiosperms can be monocotyledons or dicotyledons. The above plants can be grass plants or woody plants.

Examples of the monocotyledons encompass Orchidaceae (e.g., boat orchid, moth orchid, and vanilla), Poaceae (e.g., rice, wheat, barley, rye, corn, proso millet, foxtail millet, and sugar cane), Cyperaceae (e.g., *papyrus*), Araceae (e.g., taro), Alismataceae (e.g., arrowhead), Liliaceae (e.g., tulip, onion, Welsh onion, garlic, garlic chive, and asparagus), Dioscoreaceae (e.g., Japanese yam), and Zingiberaceae (e.g., myoga ginger and ginger). Note that in some cases, onions, Welsh onions, garlics, and garlic chives may be classified as Amaryllidaceae, and asparaguses may be classified as Asparagaceae.

Examples of the dicotyledons encompass Asteraceae (e.g., sunflower, lettuce, burdock, garland *chrysanthemum*, and Japanese butterbur), Fabaceae (e.g., soybean, pea, adzuki bean, fava bean, and peanut), Rubiaceae (e.g., coffee bean), Lamiaceae (e.g., shiso (*Perilla frutescens* var. *crispa*), *perilla*, and Japanese mint), Euphorbiaceae (e.g., poinsettia and cassava), Malvaceae (e.g., *Gossypium* and okra), Apiaceae (e.g., carrot, parsley, and celery), Brassicaceae (e.g., Japanese radish, colza, Chinese cabbage, turnip, leaf mustard, cauliflower, cabbage, broccoli, wasabi, and radish), Rosaceae (e.g., strawberry, apple, pear, cherry, Japanese plum, and peach), Solanaceae (e.g., eggplant, tomato, red pepper, tobacco, green pepper, and potato), Chenopodiaceae (e.g., spinach), Nymphaeaceae (e.g., candock and water shield), Nelumbonaceae (e.g., lotus), Rutaceae (e.g., mandarin orange and lemon), Araliaceae (e.g., udo and Japanese angelica tree), Convolvulaceae (e.g., sweet potato), Cucurbitaceae (e.g., watermelon, melon, cucumber, bitter melon, squash, and loofah), Vitaceae (e.g., grape), Pedaliaceae (e.g., sesame), Caryophyllaceae (e.g., baby's breath and carnation), Violaceae (e.g., pansy), Primulaceae (e.g., cyclamen), and Ranunculaceae (e.g., *Clematis*). Note that in some cases, spinaches may be classified as Amaranthaceae.

The plant cells having differentiation ability can be plant cells derived from two or more species of plants. This makes it possible to produce a plant body which has characteristics of the two or more species of plants. Such a plant body may lead to an advantageous effect such as an improved resistance to environmental stress, avoidance of damage by disease and pest, an improved quality, an increased yield, or an enhanced growth.

The above also makes it possible to reduce workload for grafting. For example, the need for preparation of a scion and a stock is eliminated. Further, it becomes unnecessary to manage a plant body such that neither water nor bacteria enter the plant body through a joint between a scion and a stock. Note that it is also possible to use a plant body which has been grown by a normal method as one of a scion and a stock, and use the above-described three-dimensional body as the other one of the scion and the stock.

Furthermore, as compared to conventional grafting, a plant body can be designed with a higher degree of freedom since it is possible to form only a specific organ by using cells from a different species of plant. For example, in a case where cells from a plant having large leaves are used, it is possible to enhance growth because photosynthesis can be easily performed, or it is possible to perform photosynthesis by a smaller number of leaves. On the other hand, in a case where a plant having widely spread roots is used, nutrients can be easily absorbed. This results in an enhanced plant growth or an increased sugar content or increased nutritional value. Further, it is possible to form roots of a plant which is not originally suitable for hydroponic culture, by using cells from a plant suitable for hydroponic culture. In addition, it is also possible to use cells from a plant which is resistant to coldness or hotness or resistant to disease and pest.

For example, in an embodiment of the present invention, it is possible to form a stem part and a leaf part by using cells of a watermelon and to form roots and a portion of a stem by using cells from a squash. This makes it possible to obtain an advantageous effect which is equivalent to that obtained by grafting a scion from a watermelon on a stock from a squash.

<1-2. Three-Dimensional Body>

The "three-dimensional body" herein means a structure which is formed by stacking layers of two or more cells, which structure is formed so as to have a shape that is identical to a rough shape of a target plant body. The target plant body here can be a complete plant body which includes a root, a stem and a leaf, or alternatively, can be made of some of organs of a complete plant body. For example, according to a method of producing a plant body in accordance with an embodiment of the present invention, it is possible to form a three-dimensional body in a region corresponding to roots in a plant body whose roots have been removed and to cause the three-dimensional body to differentiate into roots.

The "shape that is identical to a rough shape of a target plant body" herein means a shape in which respective positions, directions, and/or sizes of organs and/or the number of organs is/are the same as that/those of a plant body which is a target of production. Note that the "shape that is identical to a rough shape of a target plant body" herein can encompass the shape of a three-dimensional body which includes at least one of a hollow part and a groove as described later.

The shape of the three-dimensional body can be identical to or different from a shape which a target plant species has in a case where the target plant species is produced by a normal production method or a case where the target plant species grows under natural conditions. Hereinafter, the "shape which a target plant species has in a case where the target plant species is produced by a normal production method or a case where the target plant species grows under natural conditions" will be simply referred to as "normal shape".

For example, it is possible to obtain a plant body which efficiently performs photosynthesis, by using a three-dimensional body which has larger leaves, a larger number of leaves or leaves which are arranged in a different manner as compared to the normal shape. Further, it is possible to obtain a plant body which has a high water absorption ability or a high nutrient absorption ability, by using a three-dimensional body which has thicker roots, longer roots, a larger number of roots or a thicker stem(s) as compare to the normal shape. Such a three-dimensional body can achieve an enhanced growth or increased additional value of a plant body.

Further, the three-dimensional body can be subjected to arrangement control of at least either leaves or stems. For example, in such a three-dimensional body, directions of leaves or stems can be limited to one direction or two directions. For example, leaves or stems can be arranged linearly or in an L shape. Alternatively, the three-dimensional body can be provided with a region where a larger number of leaves are present and a region where a smaller number of leaves are present. Alternatively, it is possible to control directions, arrangement, and/or the number of roots, instead of that/those of leaves. Use of such a three-dimensional body allows for high-density planting by narrowing a space between plant bodies. FIG. 1 is a view schematically illustrating a shape of a plant body in accordance with an embodiment of the present invention. (a) of FIG. 1 shows normal plant bodies each having radially developed leaves. (b) of FIG. 1 shows plant bodies whose leaf directions are limited to two directions (plant bodies each having leaves which are linearly arranged). As compared to the plant bodies illustrated in (a) of FIG. 1, the plant bodies illustrated in (b) of FIG. 1 can be planted so as to have a narrower space between the plant bodies.

Moreover, for example, in plant factories, location of light sources can be optimized by limiting directions or arrangement of leaves. In other words, since the light sources need to be provided in a specific direction(s) or at a specific position(s), it is possible to reduce initial investment and heat, light and power expenses. Further, for a supposed case where three-dimensional bodies are cultivated on multiple shelves, the three-dimensional bodies can be arranged to have a short height.

Note that in a case where the directions, arrangement, or the number of leaves, stems or roots is controlled, it is preferable to prevent photosynthesis performance or nutrient absorption ability from being decreased. For example, it is preferable to increase the surface area of each leaf instead of decreasing the number of leaves, or to increase the number of leaves instead of limiting the directions of leaves.

Further, it is also possible to control a position(s) where a flower(s) is/are developed. For example, it is possible to control a position(s) where a flower(s) is/are developed by controlling directions or arrangement of leaves, stems, or branches. For example, leaves can be arranged such that no leaf is formed in the vicinity of a tip of a stem (a position where development of a flower bud is expected). For example, leaves can be arranged such that no leaf is developed at a position which is not apart from a tip of a stem by not less than a length of a leaf of the normal shape, preferably by not less than twice the length of a leaf of the normal shape. This allows for control of a position where a fruit is developed.

In recent years, in order to reduce workload of farmers and increase efficiency of farm operations, automation of various farm operations has been promoted. One of farm operations which are the most difficult to automate here is a harvesting operation. In order to automate the harvesting operation, a detection operation and an ingathering operation are necessary. The detection operation is an operation to detect an object to be harvested, by using, for example, a stereo camera, and the ingathering operation is an operation to ingather the object to be harvested, by using, for example, a manipulator. It is a problem in all operations that in a case where a first object to be harvested is behind a leaf or a second object to be harvested, the first object may not be detected or ingathered. In other words, in a case where a first object to be harvested is behind a leaf or a second object to be harvested, the first object to be harvested may not be recognized, by image recognition, as an object to be harvested. Further, even if the first object to be harvested is recognized, the ingathering operation may not be carried out for ingathering the first object. For example, in a case where a first object to be harvested is behind a leaf or a second object to be harvested, it may be difficult to approach the first object by the manipulator while no other part is damaged. In other words, leaving the shape of a body of a plant to growth of that plant itself may hinder promotion of automation of the harvesting operation.

A method of producing a plant body in accordance with an embodiment of the present invention can provide a seedling capable of having a shape which improves workability at the time when the seedling is grown or harvested, as compared to a case where arrangement of leaves and fruits is left to natural plant growth. In other words, it is possible to provide a seedling which has a shape suitable for automation. For example, it is possible to cause fruits to be developed at a given position(s) in a case where a three-dimensional body is formed so as to have leaves, stems, or branches whose directions or arrangement is/are controlled. For example, it is possible to form a three-dimensional body which has a first region where a large number of leaves are present and a second region where a fruit(s) is/are developed and in which the first region and the second region are separated from each other in a planar direction or a height direction. For example, (c) of FIG. 1 shows plant bodies having a region α where there are many leaves and a region β where fruits are developed. This achieves easier image recognition of the fruits and easier approach to the fruits by the manipulator.

As described above, the method of producing a plant body in accordance with an embodiment of the present invention makes it possible to customize the shape of a seedling to a shape which is desired by a user. Further, the method of producing a plant body in accordance with an embodiment of the present invention is applicable to not only plants for food production but also plants for ornamental use or gifts.

<1-3. Method of Forming Three-Dimensional Body>

A method of forming the three-dimensional body is not limited to a particular method. It is only necessary to provide plant cells or the like having differentiation ability in a desired shape and to form a stack of layers of such cells or the like. The plant cells can be provided by, for example, a manipulator so as to form the stack of layers. Alternatively, the desired shape can be formed by immersing a substrate in a dispersion liquid in which plant cells are dispersed. Alternatively, the desired shape can be formed by applying or dropping the dispersion liquid onto, for example, a substrate. Such a dispersion liquid herein is also referred to as "ink". For example, it is preferable to use an ink which is obtained by dispersing, in a liquid, isolated cells or spheroids or a mixture thereof. The liquid can be, for example, water. In a case where water is used for preparation of the ink, it is possible to use pure water or an aqueous solution in which various components are dissolved.

In the forming step, the three-dimensional body is preferably formed by a dipping method, an ink jet method, or a dispenser method. This makes it possible to easily form the three-dimensional body with use of the above-described ink.

In the dipping method, it is possible to use a substrate on which a pattern for providing the plant cells has been formed in advance. The dipping method can include, for example, the steps of: immersing the substrate in the ink which fills a bath or the like; and then taking out the substrate from the ink. The substrate can be a substrate on which a pattern has been formed in advance by, for example, photolithography. The pattern includes a region where the plant cells are to be provided and a region where no plant cells are to be provided. The substrate can have a surface which is modified by, for example, atmospheric-pressure plasma as needed. With such modification, the region where the plant cells are to be provided can be made hydrophilic and the region where no plant cells are to be provided can be made water-repellent. When the substrate is dipped in the ink, the plant cells can be provided only on a desired hydrophilic-region pattern.

Figure 2:
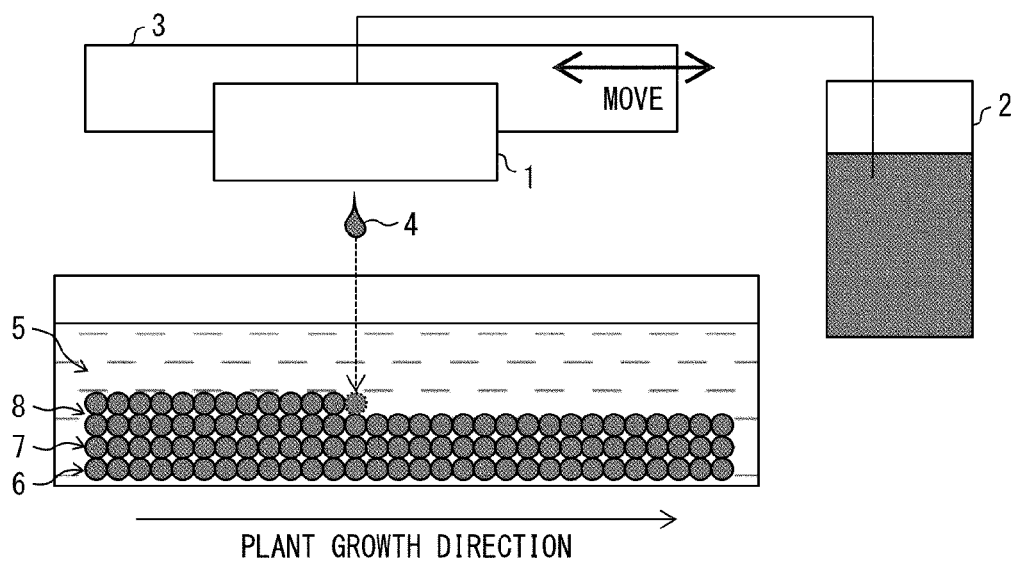
FIG. 2 is a view schematically illustrating a forming step in accordance with an embodiment of the present invention.

On the other hand, use of the ink jet method or the dispenser method makes it possible to provide the ink in a desired shape by dropping the ink on the substrate. FIG. 2 is a view schematically illustrating the forming step in accordance with an embodiment of the present invention. In FIG. 2, the ink jet method is used as an example. An ink jet head 1 is connected to a tank 2 which is filled with an ink containing the plant cells. The ink jet head 1 can be moved by a mechanism 3 for moving an ink jet head. The ink jet head 1 discharges a droplet 4 (ink which contains plant cells) while being moved. This makes it possible to form a three-dimensional body 5 including a stack of layers of the plant cells which are contained in the ink.

In a case where the ink jet method or the dispenser method is used, preferably, the plant cells are provided along a direction perpendicular to the gravitational direction (that is, along a horizontal direction). In other words, preferably, the three-dimensional body is formed such that a direction in which a stem(s) will grow in the future (plant growth direction) corresponds to the horizontal direction at the stage of the forming step. For example, as illustrated in FIG. 2, a first layer 6 is formed along the horizontal direction by dropping the droplet 4. Note that in FIG. 2, the gravitational direction is a direction in which the droplet 4 is dropped. Then, in order that the three-dimensional body 5 can have thickness, a plurality of layers such as a second layer 7 and a third layer 8 are sequentially formed on the first layer 6. This makes it possible to more simply form the three-dimensional body, as compared to a method according which plant cells are stacked along a direction parallel to the gravitational direction from the beginning. Therefore, the three-dimensional body can be formed efficiently at a high yield rate.

The above arrangement also eliminates the need to use a pattern which includes a hydrophilic region and a water-repellent region as described above. For example, the pattern can be formed by dropping the ink whose viscosity is adjusted to be high.

In the ink jet method or the dispenser method, a diameter of a nozzle for discharging the ink is determined as appropriate in accordance with a size of the plant cells which are contained in the ink. The diameter of the nozzle can be, for example, not less than 20 µm. The size of the plant cells is approximately 10 µm. Accordingly, if the diameter of the nozzle is not less than 20 µm, the risk of clogging the nozzle can be reduced. The plant cells to be discharged can be isolated cells or spheroids.

Since the ink jet method allows the ink to be discharged by the unit of picoliter to nanoliter, the ink jet method is preferable. It is preferable to use, as the ink jet method, a piezoelectric method. In the piezoelectric method, a piezoelectric element is deformed by voltage application. This causes pressure, and the ink is then discharged by the pressure. The piezoelectric method less influences the plant cells, as compared to a thermal method in which the ink is heated. Further, in the piezoelectric method, a droplet size of the ink to be discharged can be controlled to be uniform by an electric pulse signal. From this viewpoint, the piezoelectric method is preferable.

On the other hand, it is possible to use, for example, a jet dispenser method as the dispenser method. Since the jet dispenser method, like the ink jet method, is a contactless method, the jet dispenser method is suitable for forming the three-dimensional body with use of delicate cells. Further, since the jet dispenser method, like the ink jet method, allows the ink to be stably discharged in droplets of a relatively minute amount, the jet dispenser method is preferable.

In a case where the ink is used, the ink in a bath or tank can be stirred by a magnetic stirrer or bubbling. This makes it possible to keep the plant cells uniformly dispersed in the ink. Further, it is desirable to enclose a space in which the three-dimensional body formed by the ink is handled and to keep moisture inside the space at not less than 70% by, for example, a humidifier. This makes it possible to prevent the ink from drying.

In a case where the three-dimensional body is formed by using plant cells which have differentiated into a specific tissue in combination with the above-described plant cells having differentiation ability, the plant cells which have differentiated into the specific tissue is provided at a site where that tissue is to be developed (that is, cells having differentiated into a leaf are provided at a site where a leaf is to be developed, and cells having differentiated into a root are provided at a site where a root is to be developed). Further, it is preferable to provide the plant cells having differentiation ability, around the plant cells which have differentiated into the specific tissue. This arrangement makes it easier in a culture step to join (a) the plant cells which have differentiated into the specific tissue and (b) the plant cells having differentiation ability and multiplying through cell division around the plant cells which have differentiated into the specific tissue. Further, it will be possible to perform signaling from the plant cells which have differentiated into the specific tissue to the plant cells having differentiation ability around the plant cells which have differentiated into the specific tissue, so as to induce differentiation of the plant cells having differentiation ability into the specific tissue.

<1-4. Gel Beads>

In the forming step, it is preferable that the plant cells are encapsulated in gel beads, respectively. In other words, in the forming step, it is preferable to arrange the gel beads respectively containing the plant cells, in a shape that is identical to a rough shape of a target plant body. This makes it possible to easily form the three-dimensional body by stacking layers of the gel beads. The gel beads preferably contain an alkaline-earth metal salt of alginic acid (e.g., calcium alginate and barium alginate).

Figure 3:
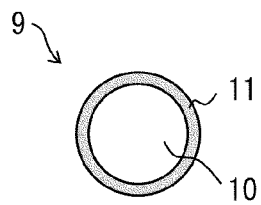
FIG. 3 is a view schematically illustrating a gel bead in accordance with an embodiment of the present invention.

A method of forming the gel beads is not limited to a particular method. For example, the gel beads can be formed by dropping an ink which contains an alginate and a plant cell having differentiation ability, into an aqueous solution of alkaline-earth metal salt. The following will describe a specific example. First, an ink is prepared, which ink contains sodium alginate and a plant cell having differentiation ability. The ink is dropped into a bath which is filled with an aqueous solution of calcium chloride which is separately prepared. The sodium alginate contained in the ink which has been dropped reacts with the calcium chloride in the bath to form a gel film of calcium alginate. In a case where an aqueous solution of barium chloride is used here in place of the aqueous solution of calcium chloride, a gel film of barium alginate is formed. This gelatinizes the surface of the ink which has been dropped, and forms a gel bead containing a plant cell and a solution. FIG. 3 is a view schematically illustrating a gel bead in accordance with an embodiment of the present invention. In a gel bead 9, an ink component 10 (which may contain a plant cell) is covered by a gel film 11. The three-dimensional body can be formed by stacking layers of the gel bead 9.

The ink can be dropped preferably by, for example, an ink jet method or a jet dispenser method which allows a small amount of droplet to be dropped. This makes it possible to minimize the size of the gel bead formed.

The ink contains the alginate at a concentration of preferably 0.5% by weight to 1.5% by weight. The aqueous solution into which the ink is dropped contains alkaline-earth metal ions at a concentration of preferably 30 mM to 180 mM, more preferably 45 mM to 90 mM.

Figure 4:
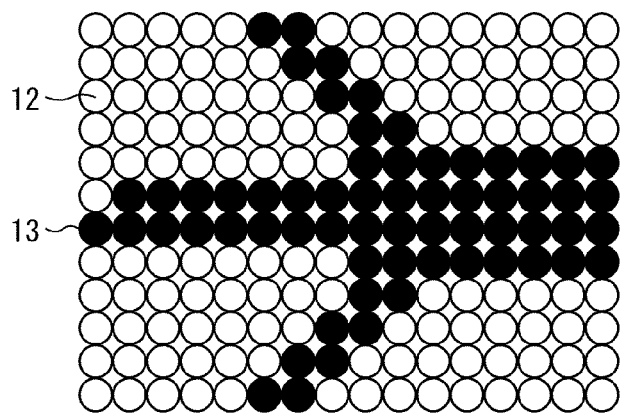
FIG. 4 is a view schematically illustrating an arrangement of gel beads in accordance with an embodiment of the present invention.

Further, in the forming step, it is possible to additionally use gel beads containing no plant cell having differentiation ability. In other words, preferably, the three-dimensional body is formed from (a) gel beads respectively containing the plant cells having differentiation ability and (b) gel beads containing no plant cell having differentiation ability. The gel beads containing no plant cell having differentiation ability can be formed in the same manner as the gel beads respectively containing the plant cells having differentiation ability. FIG. 4 is a view schematically illustrating an arrangement of gel beads in accordance with an embodiment of the present invention. As illustrated in FIG. 4, gel beads 12 containing no plant cell can be used to support gel beads 13 each containing a plant cell, which gel beads 13 are arranged in the same shape as a plant body. In other words, the gel beads 12 containing no plant cell can be used as a support material.

Figure 5:
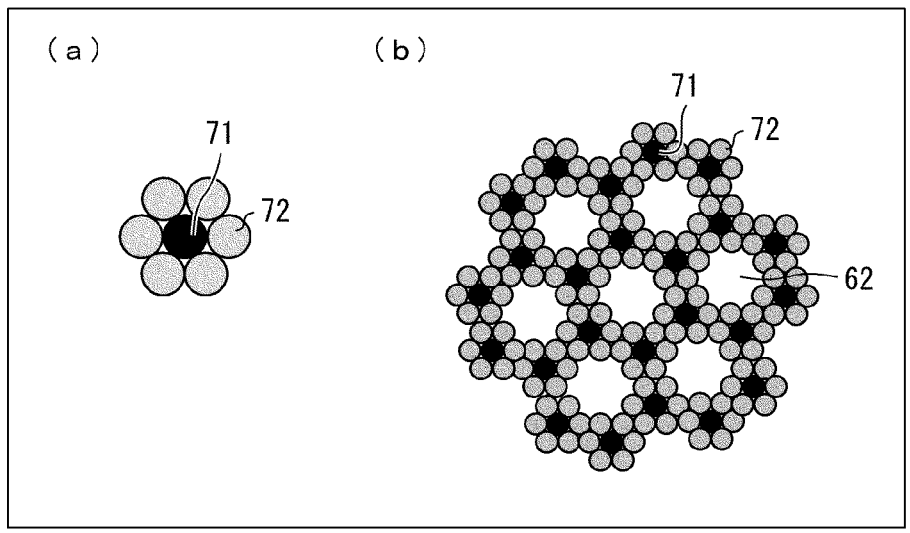
FIG. 5 is a view schematically illustrating an arrangement of gel beads in accordance with another embodiment which is different from that illustrated in FIG. 4.

Further, the gel beads containing no plant cell having differentiation ability can be gel beads respectively containing plant cells which have differentiated into a specific tissue. FIG. 5 is a view schematically illustrating an arrangement of gel beads in accordance with another embodiment which is different from that illustrated in FIG. 4. For example, as illustrated in (a) of FIG. 5, gel beads 72 respectively containing plant cells having differentiation ability can be provided so as to surround a gel bead 71 containing a plant cell which has differentiated into a specific tissue. By using the arrangement of the gel beads illustrated in (a) of FIG. 5 as the smallest unit, gel beads can be arranged as illustrated in (b) of FIG. 5. This promotes joining of plant cells as described above, and also allows for signaling from plant cells which have differentiated. Note that in the arrangement illustrated in (b) of FIG. 5, a hollow part 62 is provided. The hollow part 62 will be described later.

The gel beads have, for example, an intended function to retain a structure as the three-dimensional body. At a stage in which the function or the like becomes unnecessary, it is preferable to remove the gel beads. In a case where the gel beads are formed from the alkaline-earth metal salt of alginic acid, the gel beads can be removed by using a chelating agent which traps alkaline-earth metal ions.

<1-5. Three-Dimensional Body which Includes at Least One of Hollow Part and Groove>

The three-dimensional body can include at least one of a hollow part and a groove which are open at a surface of the three-dimensional body. In a case where oxygen and culture fluid are not sufficiently supplied to the inside of the three-dimensional body in the culture step (described later), cells inside the three-dimensional body may die. In particular, in a case where the three-dimensional body is large (for example, a case where a diameter of a part corresponding to a stem or a root is large or a case where a part corresponding to a leaf has a large thickness), the cells inside the three-dimensional body may die. In a case where the three-dimensional body includes a hollow part or a groove, oxygen and culture fluid can be supplied inside the three-dimensional body via the hollow part or the groove. For example, in a case where the part corresponding to a stem has a diameter of not less than several hundred micrometers, it is preferable to provide the hollow part or the groove. The diameter of the hollow part is preferably not less than approximately 100 µm, in view of the size of molecules passing through the hollow part and a channel resistance in the hollow part.

Figure 6:
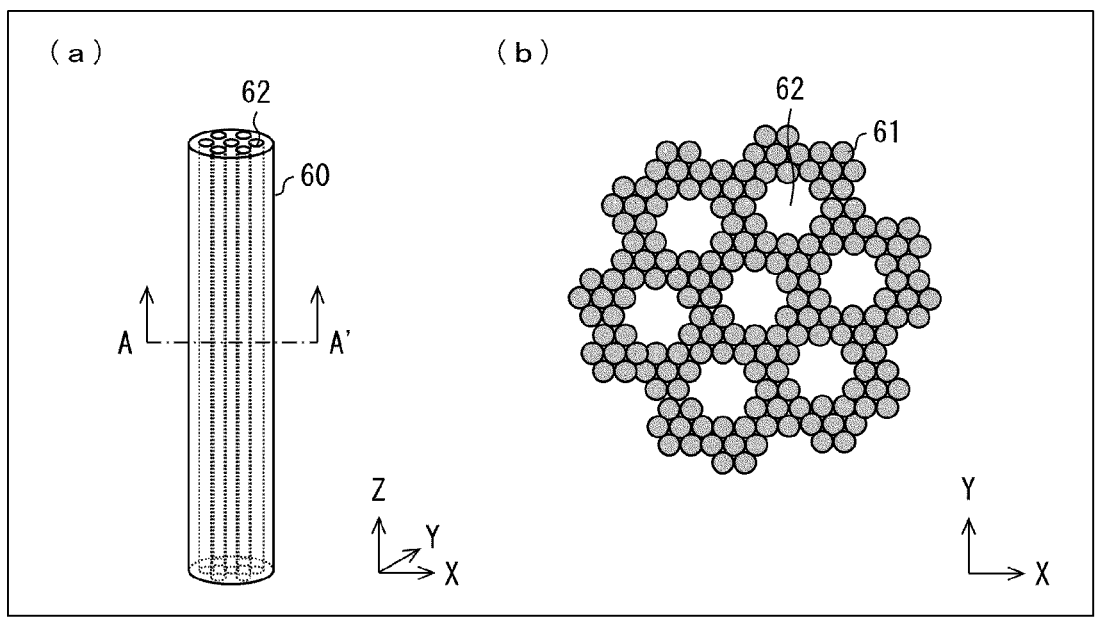
FIG. 6 is a view schematically illustrating a three-dimensional body including a hollow part in accordance with an embodiment of the present invention.

The following will describe an example in which the hollow part is provided in the part corresponding to a stem (hereinafter, simply referred to as "stem part"). FIG. 6 is a view schematically illustrating a three-dimensional body including a hollow part in accordance with an embodiment of the present invention. The following assumes a case where a stem part 60 having a diameter of 1000 µm is formed by stacking layers of gel beads 61, each of which contains a plant cell and has a diameter of 30 µm. (a) of FIG. 6 is a view illustrating an appearance of the stem part 60. (b) of FIG. 6 is a cross sectional view taken along line A-A' in (a) of FIG. 6. The stem part 60 is provided with a hollow part 62 which communicates with outside. The hollow part 62 is formed so as to be surrounded by the gel beads 61. In a case where the three-dimensional body is formed both above and below the stem part 60, the hollow part 62 should not be blocked.

Figure 7:
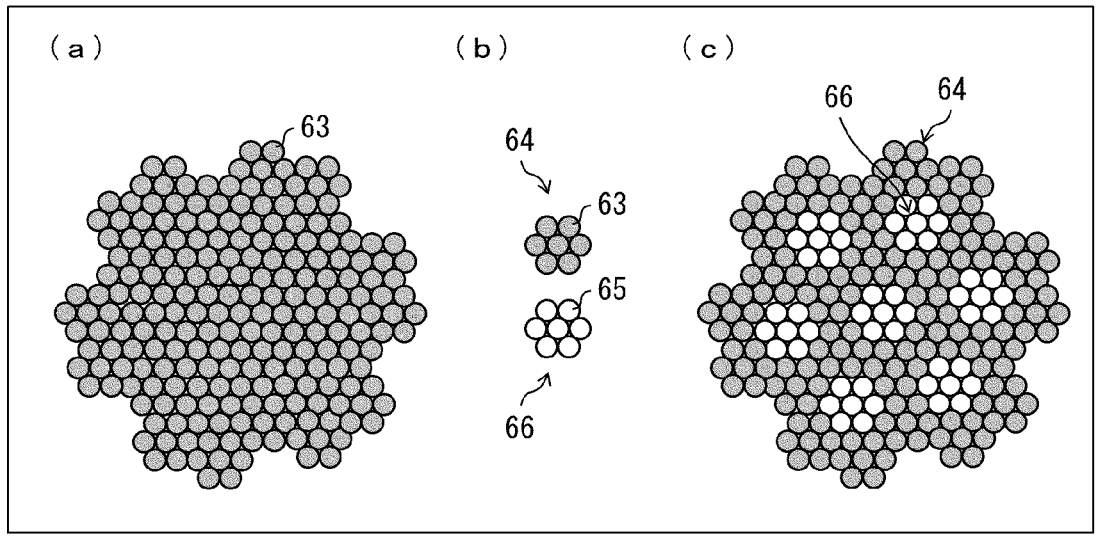
FIG. 7 is a view illustrating a model for determining an arrangement of a hollow part in accordance with an embodiment of the present invention.

FIG. 7 is a view illustrating a model for determining an arrangement of a hollow part in accordance with an embodiment of the present invention. FIG. 7 assumes the cross sectional view of (b) of FIG. 6. First, the model is prepared such that a cross section of the three-dimensional body as illustrated in (a) of FIG. 7 is formed by close packing of circles 63. The circles 63 have a diameter which is equal to that of the gel beads 61 each containing a plant cell. In consideration of a radius of the circles 63, a smallest repeat unit 64 (hereinafter, referred to as "unit 64") having a diameter of approximately 100 µm is determined. (b) of FIG. 7 shows units. In a case where the diameter of the circles 63 is 30 µm, the unit 64 is made of seven circles 63 which are closely packed. The hollow part is also configured by using a unit 66 which is made of circles 65 having the same diameter as the circles 63. (c) of FIG. 7 is a view illustrating segmentation of (a) of FIG. 7 arranged such that units 64 surround each unit 66. The units 64 are each a region where the gel beads 61 are to be provided, and the unit 66 is a region where no gel bead 61 is to be provided.

The stem part 60 including the hollow part 62 can be formed by stacking layers arranged as illustrated in (c) of FIG. 7 along a Z axis direction of (a) of FIG. 6. In this case, oxygen and culture fluid can be sufficiently supplied to all the gel beads 61 since the gel beads 61 are located in an area that is apart from the surface of the stem part 60 by not more than 50 µm. Note that it is preferable that the units 66 be provided with no gel bead from the beginning. In other words, it is not preferable to have an arrangement in which the gel beads are provided in the units 66 as a supporting material and subsequently removed afterward. Note however that the gel beads can be provided as a supporting material in parts except for the hollow part. Meanwhile, when layers of the gel beads are stacked, the ink jet method or the jet dispenser method is preferably used as described above.

Figure 8:
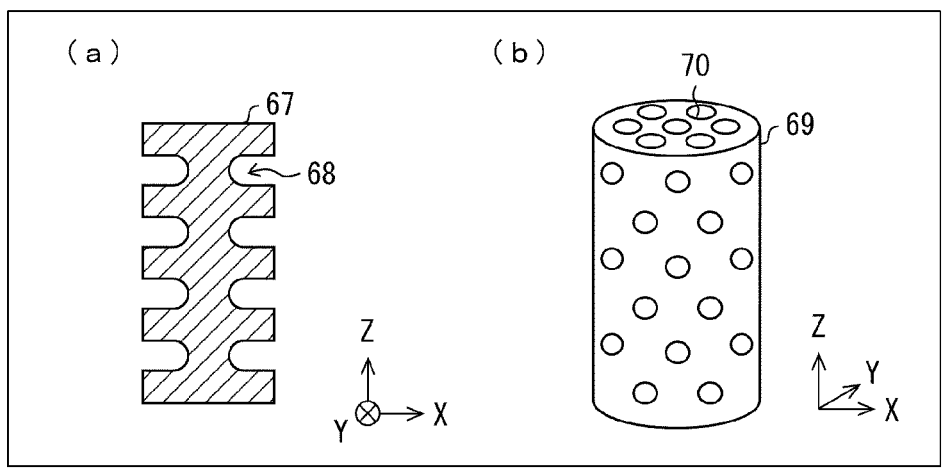
FIG. 8 is a view schematically illustrating a three-dimensional body including a hollow part in accordance with another embodiment which is different from that illustrated in FIG. 6.

The hollow part is not particularly limited in arrangement to a fluid channel communicating with a top and a bottom of the stem part (extending in the Z axis direction) as described above. For example, FIG. 8 is a view schematically illustrating a three-dimensional body including a hollow part in accordance with another embodiment which is different from that illustrated in FIG. 6. (a) of FIG. 8 shows a stem part 67 which includes a hollow part 68 perpendicular to a length direction of a stem. Note that (a) of FIG. 8 is a view of a cross section parallel to the Z axis direction. On the other hand, (b) of FIG. 8 shows a stem part 69 which includes hollow parts 70 extending in many directions and communicating with each other and which is in a sponge-like state (a porous body).

Figure 9:
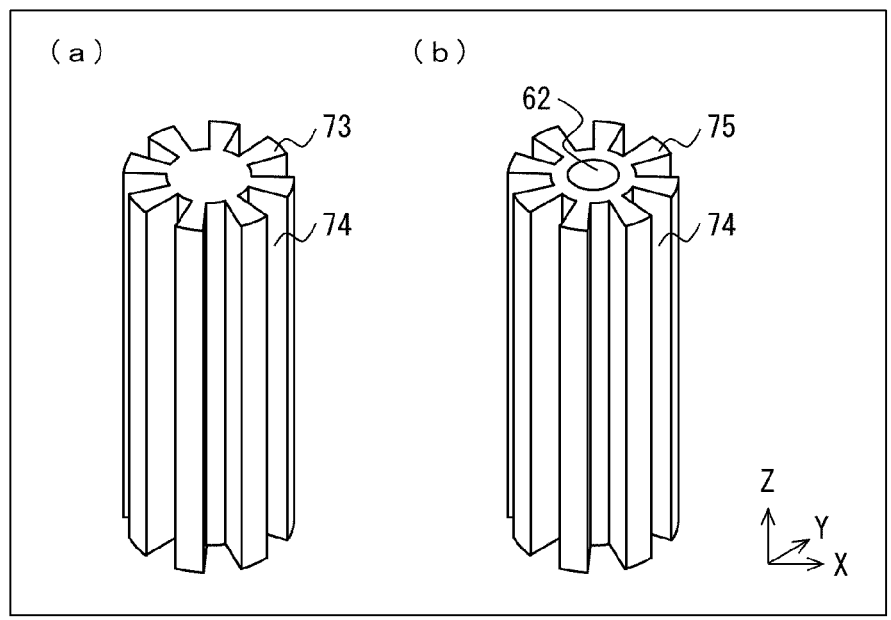
FIG. 9 is a view schematically illustrating a three-dimensional body including grooves in accordance with an embodiment of the present invention.

FIG. 9 is a view schematically illustrating a three-dimensional body including grooves in accordance with an embodiment of the present invention. For example, as illustrated in (a) of FIG. 9, grooves 74 can be provided at the surface of a stem part 73. Further, it is possible to have both the hollow part 62 and the grooves 74 as shown in a stem part 75 illustrated in (b) of FIG. 9. FIG. 9 illustrates an example of grooves, which extend in the Z axis direction (gravitational direction and length direction of the three-dimensional body). However, a direction in which the grooves extend is not limited to a particular direction. Note that in a case as illustrated in FIG. 9, it is possible to easily form the grooves extending in parallel to the length direction of the three-dimensional body by stacking layers of plant cells along a direction parallel to the gravitational direction.

The three-dimensional body which includes at least one of the hollow part and the grooves can be also formed by using the gel beads.

[2. Organization-Promoting Step]

The method of producing a plant body in accordance with an embodiment of the present invention preferably includes the step (organization-promoting step) of adding, to plant cells having differentiation ability, an organization-promoting agent containing a component that promotes organization of the plant cell, before, after or simultaneously with the forming step. This makes it possible to promote differentiation of the plant cell. For example, even in a case where the plant cells having differentiation ability for use in the forming step includes cells of a single kind, the cells can be differentiated into various organs. Further, it is possible to shorten time for obtaining a plant body from a three-dimensional body.

<2-1. Organization-Promoting Agent>

The organization-promoting agent contains a component that promotes organization of a plant cell. The organization-promoting agent can be a solid, a liquid or a gas. In view of handleability, the organization-promoting agent is preferably a liquid.

The component that promotes organization of a plant cell encompasses a growth regulator suitable for differentiation into a leaf or a root, and can be, for example, a plant hormone. Examples of the plant hormone encompass auxin and cytokinin. The following lists plant hormones. Which plant hormone is suitable for a plant cell depends on a type of the plant cell.

Examples of auxin encompass 2,4-dichlorophenoxyacetic acid (2,4-D), naphthaleneacetic acid, indolebutyric acid, indoleacetic acid, indolepropionic acid, chlorophenoxyacetic acid, naphthoxyacetic acid, phenylacetic acid, 2,4,5-trichlorophenoxyacetic acid, parachlorophenoxyacetic acid, 2-methyl-4-chlorophenoxyacetic acid, 4-fluorophenoxyacetic acid, 2-methoxy-3,6-dichlorobenzoic acid, 2-phenyl acid, picloram, and picolinic acid. Particularly, 2,4-dichlorophenoxyacetic acid, naphthaleneacetic acid, indolebutyric acid, or indoleacetic acid is preferable; 2,4-dichlorophenoxyacetic acid or naphthaleneacetic acid is more preferable; and 2,4-dichlorophenoxyacetic acid is still more preferable.

Examples of cytokinin encompass benzyladenine, kinetin, zeatin, benzylaminopurine, isopentylaminopurine, thidiazuron (TDZ), isopentenyladenine, zeatin riboside, and dihydrozeatin. Particularly, benzyladenine, kinetin, thidiazuron, or zeatin is preferable; benzyladenine, kinetin, or thidiazuron is more preferable; and thidiazuron is still more preferable.

In a case where the organization-promoting agent is used in the form of liquid, a solvent can be, for example, water. Water is preferable, because water has less influence on plant cells and water is easily handled. Note that in the present specification, a liquid containing the organization-promoting agent may also be referred to as an "ink", as with the dispersion liquid of the plant cells.

<2-2. Method of Adding Organization-Promoting Agent>

A method of adding the organization-promoting agent is not limited to a particular method, and can be, for example, the following method. In a case where the organization-promoting step is carried out prior to the forming step, the organization-promoting agent is added in advance to plant cells before the three-dimensional body is formed. In a case where the organization-promoting step is carried out after the forming step, the organization-promoting agent is added by immersing the three-dimensional body in the organization-promoting agent, or applying or dropping the organization-promoting agent to the three-dimensional body. In a case where the organization-promoting step is carried out simultaneously with the forming step, the organization-promoting agent is added to plant cells while the plant cells are provided in a desired shape.

The organization-promoting agent is added so as to produce a plant hormone environment which is suitable for a tissue to be organized. In other words, in the organization-promoting step, it is preferable to add different organization-promoting agents to two or more parts of the three-dimensional body, respectively. For example, it is preferable to add the organization-promoting agents so that the concentration of cytokinin will be high at a site where differentiation into a stem or a leaf is desired and the concentration of auxin will be high at a site where differentiation into a root is desired. For example, preferably, a weight ratio of cytokinin/auxin is in a range of 2 to 3 in the organization-promoting agent which is to be added to the site where differentiation into a leaf is desired, in a range of 1 to 2 in the organization-promoting agent which is to be added to the site where differentiation into a stem is desired, and in a range of 0.5 to 1 in the organization-promoting agent which is to be added to the site where differentiation into a root is desired.

The plant hormone environment can be adjusted by changing the amount of the organization-promoting agent to be added, depending on which site of the three-dimensional body the organization-promoting agent is to be added to. Alternatively, the plant hormone environment can be adjusted by (i) preparing in advance a plurality of organization-promoting agents different in plant hormone composition, (ii) selecting, for each site of the three-dimensional body, an organization-promoting agent from the plurality of organization-promoting agents, and (iii) adding the organization-promoting agent thus selected. In other words, in the organization-promoting step, the organization-promoting agents different in plant hormone composition can be added to two or more parts of the three-dimensional body, respectively. The expression "different in plant hormone composition" here means that each organization-promoting agent contains a single plant hormone and the single plant hormone is different in concentration in each organization-promoting agent. Further, the expression "different in plant hormone composition" also means that each organization-promoting agent contains a plurality of kinds of plant hormones and the plurality of kinds of plant hormones are different in plant hormone concentration in each organization-promoting agent. In addition, the expression "different in plant hormone composition" also means that the plant hormone(s) contained in each organization-promoting agent is/are different in kind.

In the organization-promoting step, it is preferable to add the organization-promoting agent to the three-dimensional body or the plant cells having differentiation ability, by a dipping method, an ink jet method, or a dispenser method. This makes it possible to easily add the organization-promoting agent to the three-dimensional body or the plant cells having differentiation ability. Note that this case assumes that the organization-promoting agent is used in the form of liquid.

The dipping method can include, for example, the step of immersing the three-dimensional body or the plant cells having differentiation ability in the organization-promoting agent which fills a bath. Note that in a case where the plant cells having differentiation ability is immersed in the organization-promoting agent which fills the bath, it is preferable to (i) prepare in advance a plurality of organization-promoting agents having different compositions each corresponding to a tissue into which the plant cells having differentiation ability is desired to differentiate, and (ii) to immerse the plant cells having differentiation ability into a corresponding organization-promoting agent. The ink jet method and the dispenser method can include, for example, the step of dropping the organization-promoting agent onto the three-dimensional body or the plant cells having differentiation ability. The ink jet method or the dispenser method is more preferable, from the viewpoint that an amount of the organization-promoting agent dropped is stable and easily adjustable to any amount. It is preferable to use, as the ink jet method, a piezoelectric method. The piezoelectric method allows for more stable discharge amount and easier fine control of concentration, as compared to a thermal method. As the dispenser method, it is possible to use a jet dispenser method.

Figure 10:
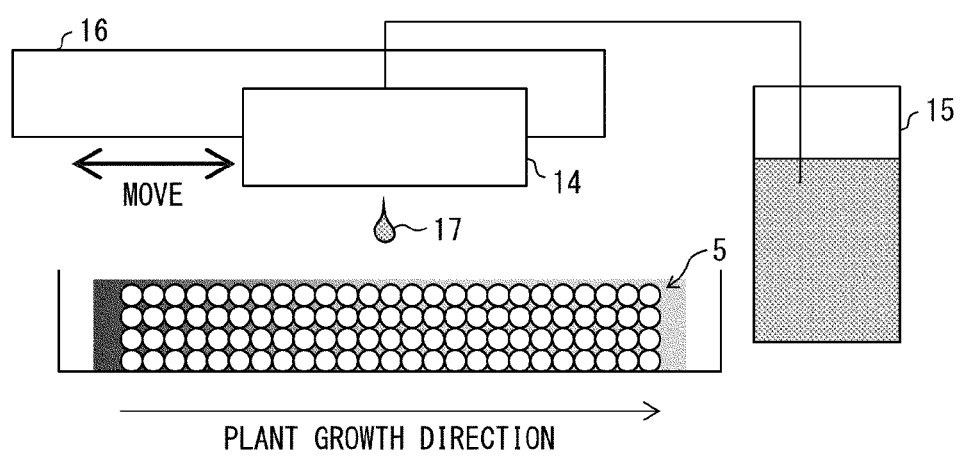
FIG. 10 is a view schematically illustrating an organization-promoting step in accordance with an embodiment of the present invention.

FIG. 10 is a view schematically illustrating the organization-promoting step in accordance with an embodiment of the present invention. FIG. 10 shows an example in which the ink jet method is used. An ink jet head 14 is connected to a tank 15 which is filled with an ink containing the organization-promoting agent. The ink jet head 14 can be moved by a mechanism 16 for moving an ink jet head. The ink jet head 14 discharges a droplet 17 (ink which contains the organization-promoting agent) while the mechanism 16 is moving the ink jet head 14. This allows the organization-promoting agent to be added to the three-dimensional body 5.

In a case where the ink jet method or the dispenser method is used, it is preferable to place the three-dimensional body along the horizontal direction and add the organization-promoting agent so that a concentration gradient is produced along the horizontal direction. In other words, it is preferable that as illustrated in FIG. 10, (i) the three-dimensional body 5 is placed such that a direction in which a stem(s) will grow in the future (plant growth direction) is along the horizontal direction at the stage of the organization-promoting step and (ii) the concentration gradient of the organization-promoting agent is produced along the plant growth direction. This makes it possible to efficiently promote differentiation of the plant cell at a high yield rate. For example, the concentration gradient is produced preferably such that the concentration of cytokinin is high at a site where differentiation into a stem or a leaf is desired and the concentration of auxin is high at a site where differentiation into a root is desired.

In the organization-promoting step, preferably, the organization-promoting agent is added to the three-dimensional body by a method capable of carrying out gradation control. For example, in the organization-promoting step, it is preferable that the ink jet method be used for gradation control. In the field of ink jet printers and the like, "gradation control" means producing color shading by continuously dropping, onto substantially identical drawing positions, a plurality of droplets of the same ink in a very short period of time. The gradation control can be carried out by continuously applying drive voltage at a high frequency. In an embodiment of the present invention, the gradation control by the ink jet method can be used to control an amount or concentration of the organization-promoting agent added. The amount or concentration of the organization-promoting agent added allows for control of a tissue organized by differentiation. Further, differentiation can be finely controlled since a continuous concentration distribution in the order of picoliter can be produced.

The piezoelectric method is an excellent method for the gradation control, and in particular, a share mode type is the best in the gradation control. The share mode type causes the ink to be discharged by (i) applying drive voltage and (ii) thereby causing a surface of a wall made of a piezoelectric element between ink chambers to be deformed into a V shape. Accordingly, an amount of deformation of the surface of the wall for discharge of the ink is small. Therefore, the share mode type allows the drive voltage to be continuously applied at a high frequency. It is known that a share mode type ink jet head is capable of controlling approximately eight gradation levels by optimization of an input waveform. The ink containing the organization-promoting agent can be used as the ink for the gradation control.

Figure 11:
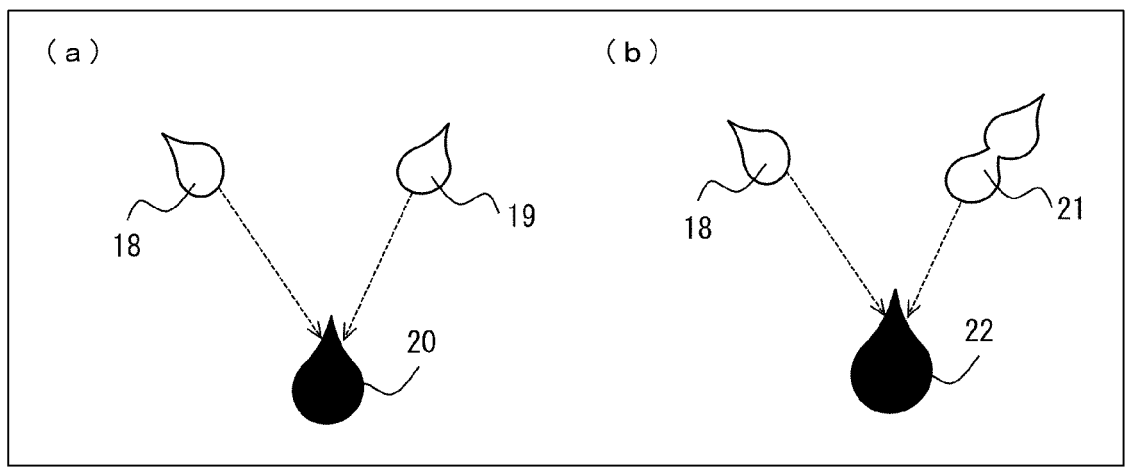
FIG. 11 is a view schematically illustrating gradation control in accordance with an embodiment of the present invention.

The gradation control can also be carried out by causing one or more droplet of ink discharged from a first nozzle to collide in the air with one or more droplet of ink discharged from a second nozzle which has a different nozzle from that of the first nozzle. FIG. 11 is a view schematically illustrating gradation control in accordance with an embodiment of the present invention. In (a) of FIG. 11, a droplet 18 corresponding to gradation level 1, which droplet is discharged from a first nozzle, is mixed with a droplet 19 corresponding to gradation level 1, which droplet is discharged from a second nozzle which is different from the first nozzle, so that a droplet 20 is obtained. In (b) of FIG. 11, a droplet 18 corresponding to gradation level 1, which droplet is discharged from a first nozzle, is mixed with droplets 21 corresponding to gradation level 2, which droplets are discharged from a second nozzle which is different from the first nozzle, so that a droplet 22 is obtained. This makes it possible to obtain the droplet 20 and the droplet 22 which have different concentrations of the organization-promoting agent, respectively.

Note that even in the case of the share mode type, a meniscus at a nozzle hole of an ink jet head becomes unstable as the gradation level is increased. This may cause deterioration in accuracy of a discharge amount or a landing position of a droplet. On this account, it is preferable to control the gradation level so that the gradation level will be approximately 3 at the highest in an application where a plurality of flying droplets are caused to collide and mix with each other in the air.

In a case where the organization-promoting step is carried out simultaneously with the forming step, it is possible to use a method according to which one droplet is formed by (i) discharging a first droplet containing a plant cell and a second droplet containing the organization-promoting agent from different nozzles, respectively, and (ii) causing the first droplet and the second droplet to collide and mix with each other in the air. Hereinafter, an ink which contains plant cells is referred to as "ink A" and an ink which contains not plant cells but the organization-promoting agent is referred to as "ink B".

The ink A should contain at least plant cells. The ink A can further contain at least one of cytokinin and auxin in addition to the plant cells. The ink B is preferably arranged to be an aqueous solution containing auxin in a case where the ink A contains cytokinin, or to be an aqueous solution containing cytokinin in a case where the ink A contains auxin. In a case where the ink A contains both of cytokinin and auxin, the ink B preferably contains at least one or both of cytokinin and auxin.

It is possible to create the optimum plant hormone environment for organization of the plant cells by mixing the ink B with the ink A. In other words, it is possible to create an environment in which the concentration of cytokinin is high at a site where differentiation into a stem or a leaf is desired, while it is possible to create an environment in which the concentration of auxin is high at a site where differentiation into a root is desired.

The optimum plant hormone environment can be created at each site after mixing the ink A and the ink B, by (i) fixing respective concentrations of the ink A and the ink B and (ii) changing a ratio of amounts of the ink A and the ink B mixed together, which ratio is changed depending on a site of the three-dimensional body to which site a resultant mixture is added. Alternatively, the optimum plant hormone environment can be created by (i) preparing in advance a plurality of concentrations of the ink A or the ink B and (ii) mixing the ink A or the ink B of a predetermined concentration depending on a site on which a resultant mixture is dropped.

Figure 12:
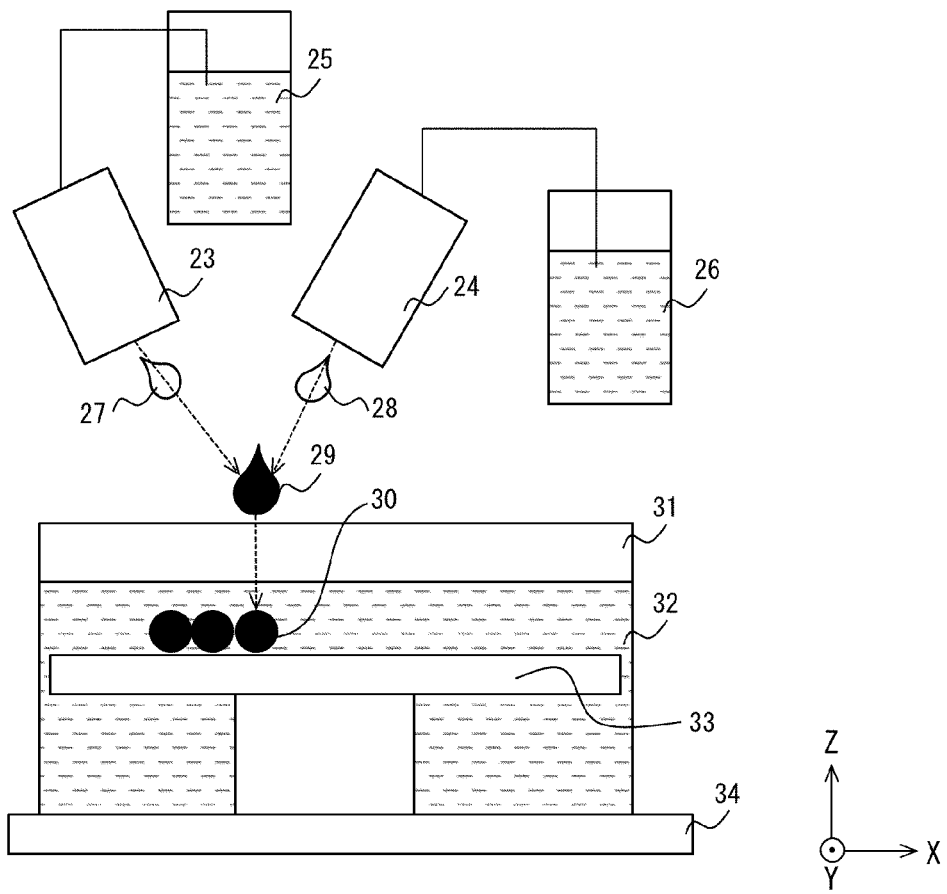
FIG. 12 is a view schematically illustrating a case where the organization-promoting step is carried out simultaneously with the forming step and where droplets are caused to collide and mix with each other in the air.

The following will discuss one example of a method of carrying out the organization-promoting step simultaneously with the forming step, with reference to FIG. 12. FIG. 12 is a view schematically illustrating a case where the organization-promoting step is carried out simultaneously with the forming step and where droplets are caused to collide and mix with each other in the air. An ink jet head 23 and an ink jet head 24 are prepared. The ink jet head 23 discharges the ink A, and the ink jet head 24 discharges the ink B. The ink jet head 23 is connected with a tank 25 which is filled with the ink A, and the ink jet head 24 is connected with a tank 26 which is filled with the ink B. When to discharge the ink A from the ink jet head 23 and when to discharge the ink B from the ink jet head 24 are controlled, so that one droplet 29 can be formed by causing a droplet 27 of the ink A and a droplet 28 of the ink B to collide with each other in the air. For example, the ink jet head 23 and the ink jet head 24 are arranged to face each other, and wave signals for discharging droplets from the ink jet head 23 and the ink jet head 24 are synchronized with each other under a condition where flying speeds of the droplets are matched with each other in advance. This allows the droplet 27 and the droplet 28 to collide and mix with each other in the air. The ink jet head 23 and the ink jet head 24 here can carry out gradation control. Accordingly, it is also possible to cause, for example, a collision between a droplet corresponding to gradation level 1 discharged from the ink jet head 23 and droplets corresponding to gradation level 2 discharged from the ink jet head 24. Note that it is desirable to prevent influence of an external disturbance such as wind on flying droplets, for example, by providing a screen around the ink jet head 23 and the ink jet head 24.

The ink A or the ink B here can contain an alginate such as sodium alginate. Meanwhile, the ink jet head 23 and the ink jet head 24 can be provided so that the droplet 29 can be dropped in an aqueous solution 32 of calcium chloride which fills a bath 31. In this case, when the droplet 29 is dropped into the aqueous solution 32 of calcium chloride, an alginic acid component in the droplet 29 and a calcium component in the tank 31 react with each other. As a result, a gel is instantly formed at a boundary between the droplet 29 and the aqueous solution 32 of calcium chloride. This results in formation of a gel bead 30 containing a component of the ink A and a component of the ink B.

While the above-described discharge is repeated, a Z-axis stage 33 and an X-Y planar stage 34 are moved. This allows for formation of the three-dimensional body by joining gel beads 30 together and stacking layers of the gel beads 30.

Note that in order to stack the layers at a high accuracy, the Z-axis stage 33 is preferably provided in the vicinity of the surface of the aqueous solution 32 of calcium chloride at the time when the forming step is started (at the time when the droplet 29 is dropped). Then, it is desirable to move the Z-axis stage 33 downward (toward a lower side of a Z axis) by a distance corresponding to a diameter of the gel bead 30, at the time when a layer of gel beads 30 is to be provided.

Figure 13:
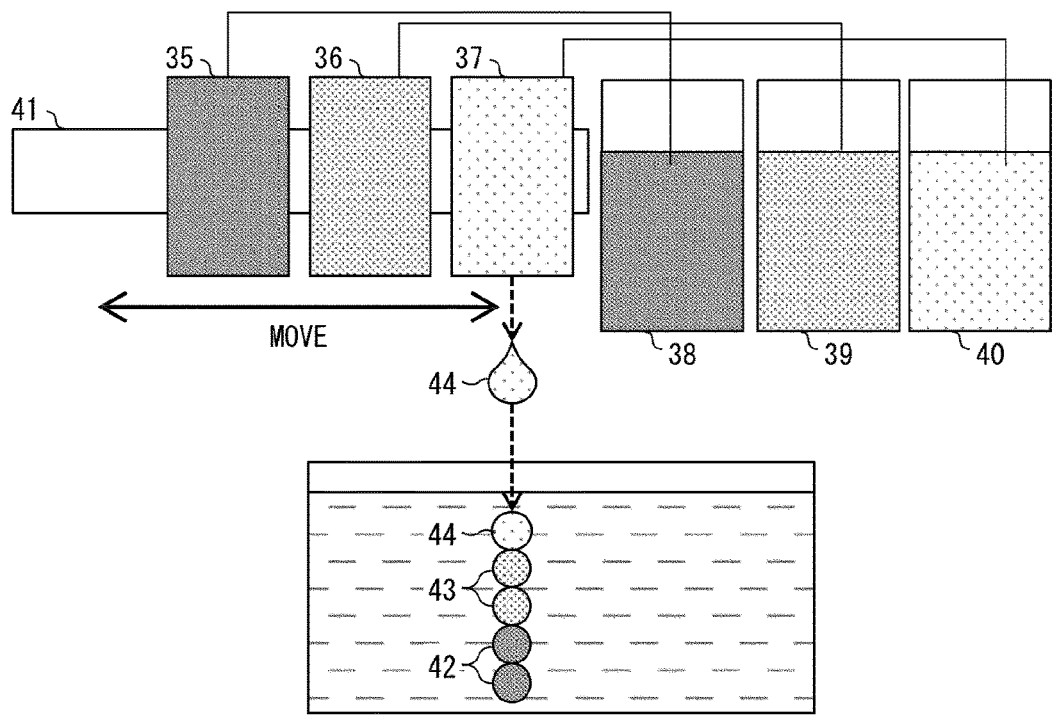
FIG. 13 is a view schematically illustrating a case where the organization-promoting step is carried out simultaneously with the forming step and where organization-promoting agents having different compositions, respectively, are used.

It is preferable to use a method in which the ink A and the ink B are caused to collide and mix with each other in the air, from the viewpoint of having a simpler device configuration. However, the method of adding the organization-promoting agent is not limited to such a method. For example, the three-dimensional body can be formed from a plurality of inks while the plurality of inks are not mixed together. In this case, the three dimensional body can be formed by (i) preparing in advance the plurality of inks, each of which inks contains (a) plant cells and (b) an organization-promoting agent having a different composition and (ii) discharging these inks from different discharging means, respectively. FIG. 13 is a view schematically illustrating a case where the organization-promoting step is carried out simultaneously with the forming step and where organization-promoting agents having different compositions, respectively, are used. FIG. 13 assumes a case using inks C, D, and E, each of which inks contains (a) plant cells and (b) an organization-promoting agent having a different composition. Ink jet heads 35, 36 and 37 are prepared. The ink jet head 35 discharges the ink C, the ink jet head 36 discharges the ink D, and the ink jet head 37 discharges the ink E. The ink jet head 35 is connected with a tank 38 which is filled with the ink C. The ink jet head 36 is connected with a tank 39 which is filled with the ink D. The ink jet head 37 is connected with a tank 40 which is filled with the ink E. The ink jet heads 35, 36 and 37 can be moved by a mechanism 41 for moving ink jet heads. After the ink jet head 35 is caused to discharge a droplet 42 of the ink C, respective positions of the ink jet heads 35, 36 and 37 are moved by the mechanism 41. Then, the ink jet head 36 is caused to discharge a droplet 43 of the ink D, so that the droplet 43 is stacked on the droplet 42 so as to form a layer. After the respective positions of the ink jet heads 35, 36 and 37 are similarly moved, the ink jet head 37 is caused to discharge a droplet 44 of the ink E, so that the droplet 44 is stacked on the droplet 43 so as to form a layer. In this case, the inks need not be mixed in the air. This achieves a more stable process. Further, it is possible to obtain gel beads by (i) arranging the plurality of inks such that each of the inks contains an alginate and (ii) dropping the inks into an aqueous solution of calcium chloride.

[3. Culture Step]

It is preferable to have the culture step after the forming step. In the culture step, the three-dimensional body is cultured and grown so as to be a target plant body. Note that preferably, the culture step is carried out after the forming step and the organization-promoting step. This makes it possible to further promote differentiation of the three-dimensional body.

The three-dimensional body formed in the forming step is, for example, put in a culture apparatus or culture fluid so as to grow into a plant body. The culture step can be carried out by aeration culture.

In the culture step, the three-dimensional body can be cultured so as to be joined to another plant body. In the above-described forming step, the three-dimensional body can be formed so that a plant body containing all of organs including, for example, leaves, a stem(s), and roots. However, it is not necessary to form all the organs in the forming step. It is possible to culture a three-dimensional body capable of becoming one or some of organs of a plant body so that the three-dimensional body will be joined to a plant body which is arranged in advance to lack the one or some of organs. For example, a three-dimensional body is joined to a plant body which lacks roots, and then, the three-dimensional body can be caused to differentiate into roots. For example, in Examples described later, a three-dimensional body was formed, by using inks containing strawberry cells, for a strawberry seedling from which roots had been removed.

Note that in a case where the three-dimensional body is cultured so as to join to another plant body, the three-dimensional body and the another plant body can be the same or different in plant species. For example, a root part of a watermelon can be formed by using squash cells, for the watermelon from which the root part has been removed. This makes it possible to form squash roots which are joined to a stem of the watermelon. Then, it becomes possible to form a plant body which is equivalent to that obtained by grafting a scion from a watermelon on a stock from a squash. It is also possible to form only a root part of a plant which is not suitable for hydroponic culture, by using cells from a plant body suitable for hydroponic culture. This allows for hydroponic culture of a plant which is typically unsuitable for hydroponic culture.

In the culture method, it is preferable that a length direction of a part of the three-dimensional body which part corresponds to a stem be kept parallel to the gravitational direction. Note that the "length direction of a part of the three-dimensional body which part corresponds to a stem" is intended to mean a direction in which the stem of a plant body will grow. In other words, it is preferable that the three-dimensional body be cultured while being kept such that a direction in which a stem(s) will grow is an upward direction along the gravitational direction and a direction in which roots will grow is a downward direction along the gravitational direction. In this way, the three-dimensional body is cultured in a gravitational environment which is same as that of a plant which grows in nature. This makes it possible to prevent the plant body from growing in an unintended direction. In a case where the three-dimensional body which is, for example, a leaf or a root is to be joined to another plant body which has a stem, preferably, a direction in which the stem of the another plant will grow is kept to be parallel to the gravitational direction.

Figure 14:
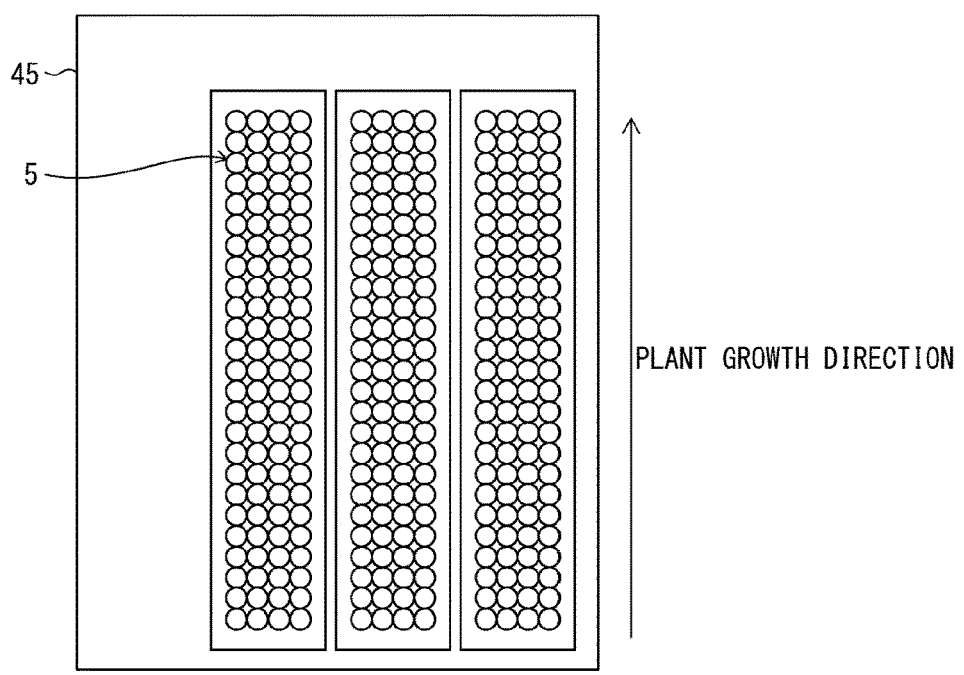
FIG. 14 is a view schematically illustrating a culture step in accordance with an embodiment of the present invention.

FIG. 14 is a view schematically illustrating the culture step in accordance with an embodiment of the present invention. In FIG. 14, the three-dimensional body 5 is kept in a culture apparatus 45 such that a direction in which a stem(s) will grow in the future (plant growth direction) is parallel to the gravitational direction.

The present invention is not limited to the embodiments, but can be altered by a skilled person in the art within the scope of the claims. The present invention also encompasses, in its technical scope, any embodiment derived by combining technical means disclosed in differing embodiments.

EXAMPLES

The following will discuss an embodiment of the present invention in more detail with reference to Examples. Note, however, that the present invention is not limited to such Examples.

Example 1

<Ink Preparation>

First, cells for use in a forming step were prepared as below. A lamina of strawberry (variety: "Tochiotome") was collected. Then, the lamina was disinfected and sterilized by a general method using ethanol and sodium hypochlorite. Further, 1/3 MS medium was prepared by 3-fold dilution of an inorganic composition of MS medium. With respect to the 1/3 MS medium, 30 g/L of sucrose, 1.0 mg/L of TDZ, and 0.1 mg/L of 2,4-D were added. A resultant medium was used to perform callus induction from the lamina. Each cell of a callus thus obtained was isolated by using an aqueous solution of cellulase.

The each cell isolated was dispersed in an aqueous solution having a TDZ concentration which had been adjusted to 1.0 mg/L. As a result, an ink A-1 was obtained. Further, three kinds of aqueous solutions of 2,4-D were prepared. An aqueous solution having a 2,4-D concentration of 0.2 mg/L was referred to as "ink B-1", an aqueous solution having a 2,4-D concentration of 0.4 mg/L was referred to as "ink B-2", and an aqueous solution having a 2,4-D concentration of 0.6 mg/L was referred to as "ink B-3".

<Preparation of Substrate for Use in Forming Step>

Figure 15:
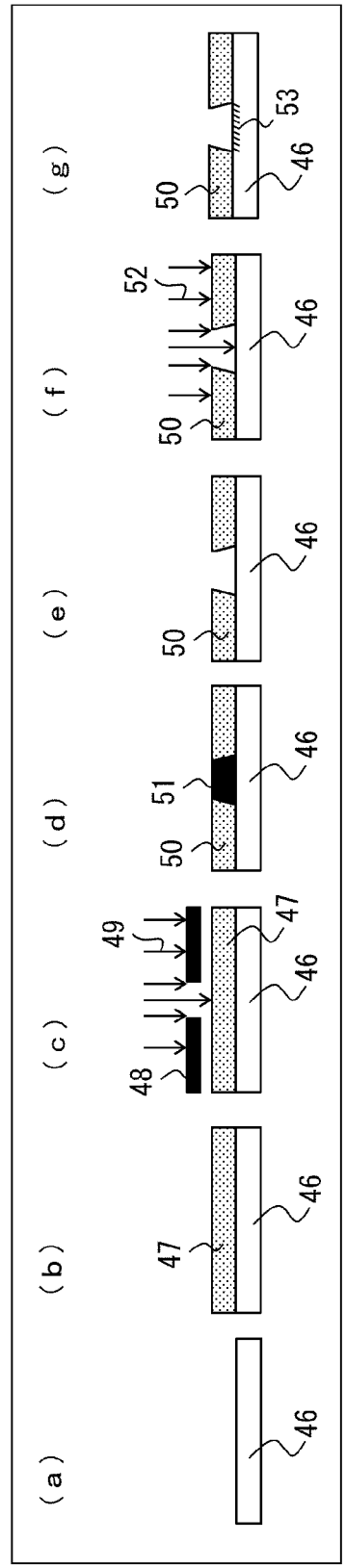
FIG. 15 is a view schematically illustrating a method of fabricating a substrate for use in Example 1.

Next, a substrate, on which a pattern was formed, was prepared as below. This substrate was used in the forming step. FIG. 15 is a view schematically illustrating a method of fabricating a substrate for use in Example 1. First, as illustrated in (a) and (b) of FIG. 15, a positive photoresist 47 was applied to a glass substrate 46 by using a slit coater. As illustrated in (c) of FIG. 15, the positive photoresist 47 was masked by a metal mask 48 having an aperture pattern which allows cells to be provided in a desired pattern. Then, the positive photoresist 47 was irradiated with light 49 for exposure. As a result, a photoresist layer 50 was formed as illustrated in (d) of FIG. 15. Subsequently, as illustrated in (d) and (e) of FIG. 15, an exposed part 51 was removed by using an etching liquid (aqueous solution of tetramethylammonium hydroxide). Thereafter, the glass substrate 46 on which the pattern was formed was subjected to hydrophilization as illustrated in (f) of FIG. 15. In the hydrophilization, the glass substrate 46 was treated with plasma 52 by use of an ashing apparatus. This allowed for obtaining the glass substrate 46 having a hydrophilic region 53 as illustrated in (g) of FIG. 15. Note that conditions of a plasma treatment were adjusted so that a contact angle with respect to water would be not more than 10° in a region where cells were to be provided (a part from which the photoresist layer 50 was removed) and a contact angle with respect to water would be not less than 60° in a region where the cells were not to be provided (a part where the photoresist layer 50 remained).

<Forming Step>

Figure 16:
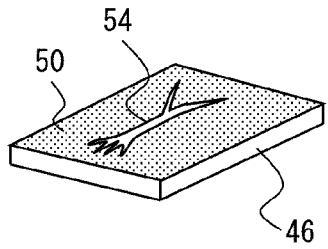
FIG. 16 is a view schematically illustrating a substrate for use in Example 1.

The substrate on which the pattern was formed as described above was dipped in the ink A-1 which filled a bath, and then taken out from the bath. FIG. 16 is a view schematically illustrating a substrate for use in Example 1. The above dipping allowed an ink 54 (ink A-1) to be provided only on a predetermined pattern as illustrated in FIG. 16.

<Organization-Promoting Step>

Next, in an organization-promoting step, the inks B-1, B-2, and B-3 were dropped by using a dispenser onto the ink A-1 provided on the substrate, so that the ink A-1 was covered with the inks B-1, B-2, and B-3. The inks B-1, B-2, and B-3 were dropped here such that (i) the ink B-1 was dropped on a part which was supposed to be a root of a plant body after culturing, (ii) the ink B-2 was dropped on a part which was supposed to be a stem of the plant body after culturing, and (iii) the ink B-3 was dropped on a part which was supposed to a leaf of the plant body after culturing. In order to cover the ink A-1 present on the pattern, the inks B-1, B-2, and B-3 were dropped such that a total amount of the inks dropped was double that of the ink A-1. Note that in order to prevent the inks B-1, B-2, and B-3 from mixing together on the substrate, fluidities of the inks B-1, B-2, and B-3 were suppressed by adjusting viscosities of the inks B-1, B-2, and B-3.

<Culture Step>

Following the organization-promoting step, a culture step was carried out. In the culture step, a sample which had been prepared in the organization-promoting step was put in a culture fluid containing sucrose and the like, and aeration culture was carried out. The aeration culture was carried out for 45 days under controlled conditions where the light intensity was 40 $\mu mol \cdot m^{-2} \cdot sec^{-1}$, the day length was 16 hours, and the temperature was 25° C.

Example 2

<Ink Preparation>

Cells were isolated as in Example 1. The cells isolated were dispersed in an aqueous solution, which had been adjusted such that a sodium alginate concentration was 1% by weight and a TDZ concentration was 2.4 mg/L. As a result, an ink A-2 was obtained. Further, an aqueous solution having a 2,4-D concentration of 1.0 mg/L was prepared as an ink B-4.

<Configuration of Apparatus>

An apparatus for use in Example 2 was configured in a similar manner as that illustrated in FIG. 12. An ink jet head for discharging the ink A-2 and an ink jet head for discharging the ink B-4 were separately prepared, and arranged so as to be inclined at approximately −30° to 30° with respect to a vertical direction. This allowed one droplet to be formed by causing a collision of a droplet of the ink A-2 and a droplet of the ink B-4. These two ink jet heads were each a piezoelectric share-mode-type ink jet head capable of carrying out gradation control.

Further, below these two ink jet heads, a bath which was filled with 2% by weight aqueous solution of calcium chloride was placed. Furthermore, a Z-axis stage was provided in the bath, and an X-Y planar stage was provided below the bath.

<Forming Step and Organization-Promoting Step>

In Example 2, the forming step and the organization-promoting step were carried out simultaneously by using the above apparatus. Note that in Example 2, a discharge amount of ink from each of the ink jet head was set to approximately 7 µL per droplet, and that in the case of gradation level 2, the discharge amount was approximately 14 µL per droplet and in the case of gradation level 3, the discharge amount was approximately 20 µL per droplet. In Example 2, the ink jet head discharging the ink A-2 was always arranged to discharge a droplet corresponding to gradation level 1, and the ink jet head discharging the ink B-4 was arranged to discharge a droplet(s) corresponding to gradation level 1 to 3. Therefore, when the droplets discharged from these two ink jet heads were mixed together to form a droplet, the amount of the droplet thus formed became 14 µL to 27 µL. A gel bead formed from this droplet had a diameter of 30 µm to 40 µm. The ink B-4 corresponding to gradation level 1 was dropped on a part which was supposed to be a leaf of a plant body after culturing. Meanwhile, the ink B-4 corresponding to gradation level 2 was dropped on a part which was supposed to be a stem of the plant body after culturing. Further, the ink B-4 corresponding to gradation level 3 was dropped on a part which was supposed to a root of the plant body after culturing. A resultant weight ratio of TDZ and 2,4-D, which were contained in the gel bead prepared as described above, was shown in Table 1 below.

TABLE 1

| Part organized by culturing | Leaf | Stem | Root |
|---|---|---|---|
| Gradation level of ink B-4 | 1 | 2 | 3 |
| Amount of mixed inks (pL) | 14 | 21 | 27 |
| TDZ concentration (mg/L) | 1.2 | 0.8 | 0.7 |
| 2,4-D concentration (mg/L) | 0.5 | 0.7 | 0.84 |
| Weight ratio (TDZ/2,4-D) | 2.4 | 1.2 | 0.8 |

While gel beads were being formed, the X-Y planar stage and the Z-axis stage were moved. As a result, 15 to 16 layers of the gel beads were stacked. The three-dimensional body was ultimately formed to have a size of approximately 10 cm in length, 1 cm in width, and 0.5 cm in thickness. Here, the length means a length in an X axis direction, the width means a length in a Y axis direction, and the thickness means a length in a Z axis direction.

<Culture Step>

Subsequently, in a culture step, the three-dimensional body thus formed was put in a culture fluid containing sucrose and the like, and aeration culture was carried out. The aeration culture was carried out for 45 days under controlled conditions where the light intensity was 40 $\mu mol \cdot m^{-2} \cdot sec^{-1}$, the day length was 16 hours, and the temperature was 25° C.

Additionally, a new three-dimensional body sample was prepared by the same method. Then, the culture step was similarly carried out while this sample was kept such that a part which was supposed to be a root of a plant body was on a lower side and a part which was supposed to be a leaf of the plant body was on an upper side.

Example 3

Figure 17:
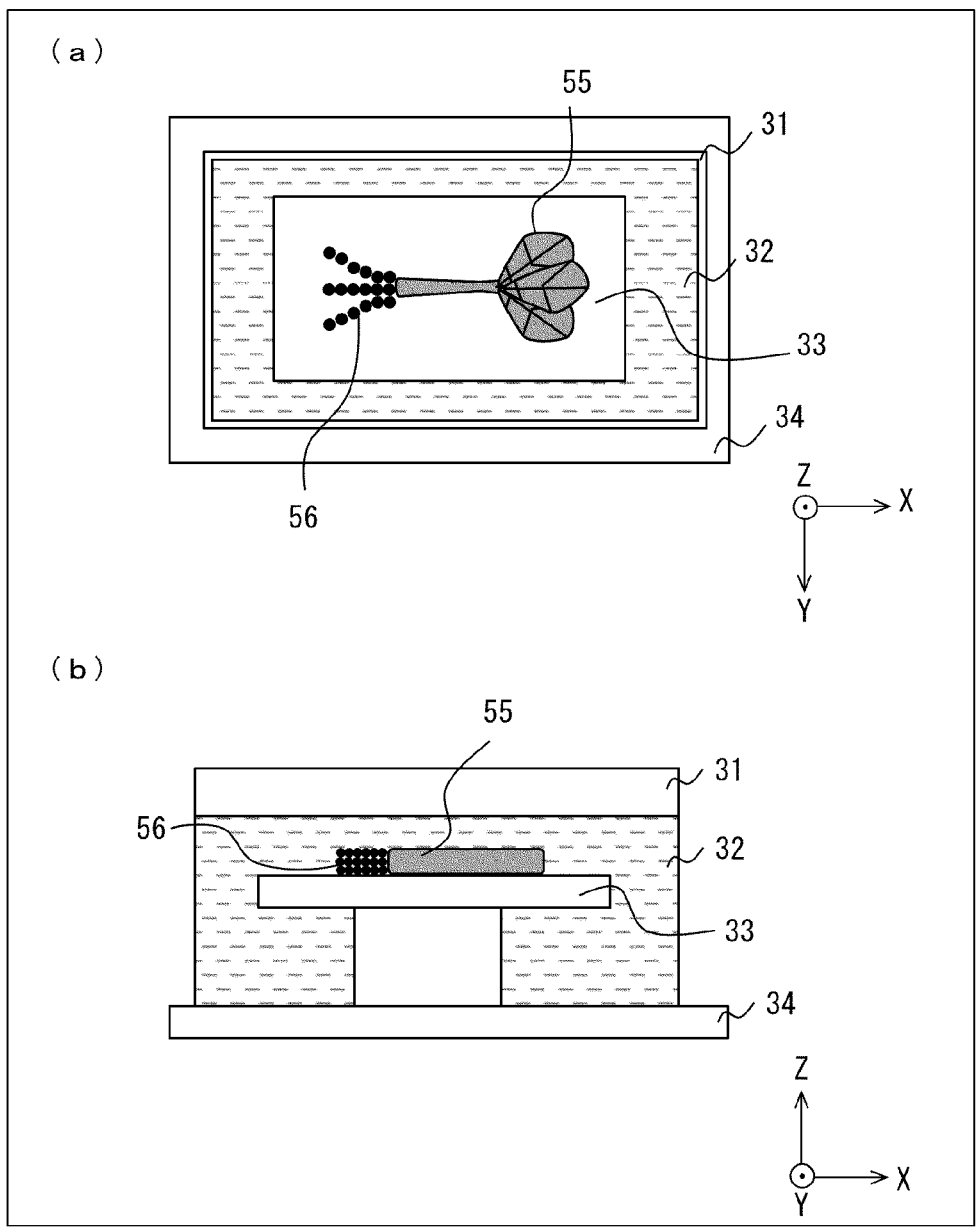
FIG. 17 is a view schematically illustrating the forming step in Example 3.

First, collected cells were cultured and an ink A-3 and an ink B-5 were prepared, as in Example 2. Further, an apparatus which was configured in the same manner as that illustrated in FIG. 12 was used in Example 3. FIG. 17 is a view schematically illustrating the forming step in Example 3. In Example 3, as illustrated in FIG. 17, a strawberry seedling 55 (total length: approximately 7 cm) from which roots had been removed was put and fixed in a tank 31 which was filled with an aqueous solution 32 of calcium chloride. Then, gel beads 56 were formed so as to be continuous with the strawberry seedling 55 in a part from which the roots had been removed As a result, a three-dimensional body was prepared. Note that (a) of FIG. 17 is a view from a position in a Z axis direction and (b) of FIG. 17 is a view from a position in a Y axis direction. In this case, a discharge amount of ink from the ink jet head 23 was set to approximately 7 µL per droplet, and this discharge amount corresponded to gradation level 1. Meanwhile, a discharge amount of ink from the ink jet head 24 per droplet was set to approximately 7 µL. Since the gradation level was 3, the discharge amount from the ink jet head 24 was set to approximately 20 µL.

Figure 18:
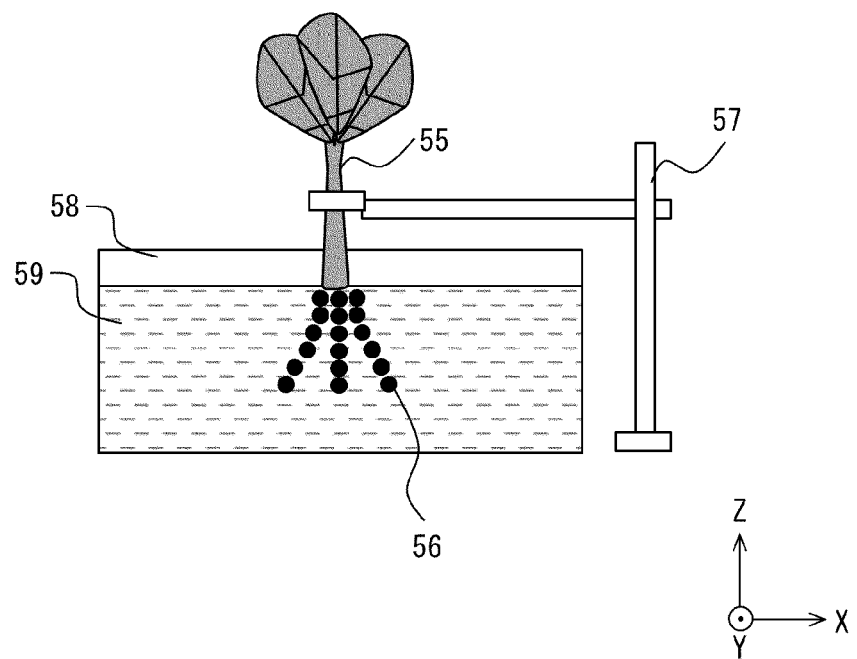
FIG. 18 is a view schematically illustrating the culture step in Example 3.

FIG. 18 is a view schematically illustrating the culture step in Example 3. A plant body including the three-dimensional body prepared as described above was arranged as illustrated in FIG. 18 by using a clamp 57 such that a part which was supposed to be a root of a plant body after culturing was on a lower side in the gravitational direction. Note that culturing was carried out while the plant body was kept such that only the three-dimensional body formed by the gel beads 56 was in a culture fluid 59 with which a container 58 was filled. This arrangement was intended to prevent contamination in culturing, and also takes into account influence of the gravity on differentiation. Thereafter, culturing was carried out for 15 days under the same conditions as those in the culture step in Example 2.

Example 4

Cells were isolated as in Example 1. Isolated plant cells having differentiation ability were separated into four groups. With respect to each of three groups among the four groups, a corresponding one of respective blends of organization-promoting agents (see Table 2 below), sucrose, and the like were added. Inks C-1, C-2, and C-3 were thus prepared. The blends were suitable for differentiation into leaves, stems, and roots, respectively. Plant cells in remaining one of the four groups of the isolated plant cells having differentiation ability were dispersed in a 1% by weight aqueous solution of sodium alginate, so that an ink D-4 was prepared.

TABLE 2

| Ink | C-1 | C-2 | C-3 |
| --- | --- | --- | --- |
| TDZ concentration (mg/L) | 1.2 | 0.8 | 0.7 |
| 2,4-D concentration (mg/L) | 0.5 | 0.7 | 0.84 |

Next, after the inks C-1, C-2, and C-3 were subjected to aeration culture for 3 days, sodium alginate was added to each of the inks C1, C-2, and C-3 such that 1% by weight of the sodium alginate was contained. Inks D-1, D-2, and D-3 were thus prepared. Further, a 1% by weight aqueous solution of sodium alginate was prepared as an ink D-5 for a supporting material which contained no plant cell.

Respective droplets of the inks D-1 to D-5 were dropped into the 2% by weight aqueous solution of calcium chloride, by using five ink jet heads. The discharge amount of ink per droplet was set to approximately 7 µL. In this case, gel beads formed had a diameter of approximately 20 µm.

The inks D-1 and D-4 were dropped on a part where a leaf was to be formed, the inks D-2 and D-4 were dropped on a part where a stem was to be formed, and the inks D-3 and D-4 were dropped on a part where a root was to be formed. Further, the ink D-5 was dropped on a part where the supporting material was necessary. The ink D-4 was dropped so as to form gel beads, around the gel beads which had been formed by dropping the inks D-1, D-2, or D-3. In the above arrangement, in the culture step, the plant cells having differentiation ability (ink D-4), which has not undergone the organization-promoting step, multiplies through cell division, and functions to join plant cells in adjacent gel beads. On the other hand, the plant cell (inks D-1, D-2, and D-3), which has undergone the organization-promoting step and differentiated, joins to the plant cells having differentiation ability around that plant cell having differentiated. At this time, the plant cell (inks D-1, D-2, and D-3) functions to perform signaling for inducing differentiation of the plant cells having differentiation ability into specific tissues.

While gel beads were being formed, the X-Y planar stage and the Z-axis stage were moved. As a result, 15 to 16 layers of the gel beads were formed. The three-dimensional body was thus obtained. The three-dimensional body ultimately formed had a size of approximately 5 cm in length, 1 cm in width, and 0.3 cm in thickness. Here, the length means a length in an X axis direction, the width means a length in a Y axis direction, and the thickness means a length in a Z axis direction.

Thereafter, the culture step was carried out as in Example 2. Note that although only the plant cells having differentiation ability was used as materials in Example 4, differentiated plant cells having been extracted from plant tissues can be also used. A similar effect can be obtained, in a case where the ink D-1 (leaf), the ink D-2 (stem) and the ink D-3 (root) are prepared by isolating and dispersing such differentiated plant cells having been extracted from plant tissues and the same process as described above is carried out.

INDUSTRIAL APPLICABILITY

An aspect of the present invention is applicable to, for example, production of a plant body having a shape that is suitable for plant growing or plant cultivation.

REFERENCE SIGNS LIST 1, 14 ink jet head
2, 15 tank
3, 16 mechanism for moving an ink jet head(s)
4, 17 droplet
5 three-dimensional body
9 gel bead
10 ink component
11 gel film
12 gel bead containing no plant cell
13 gel bead containing a plant cell

The invention claimed is:
1. A method of producing a plant body, comprising the steps of:
forming a three-dimensional body which contains plant cells having differentiation ability and which includes at least one of a hollow part and a groove which are open at a surface of the three-dimensional body;
adding an organization-promoting agent to the three-dimensional body or the plant cells having differentiation ability, the organization-promoting agent containing a component that promotes organization of the plant cells, the step of adding the organization-promoting agent being carried out before, after or simultaneously with the step of forming the three-dimensional body; and culturing the three-dimensional body, after the step of forming the three-dimensional body and the step of adding the organization-promoting agent, wherein the culturing of the three dimensional body includes the step of supplying oxygen and culture fluid to the three dimensional body, and wherein, in the step of forming the three-dimensional body, gel beads containing the plant cells having differentiation ability are arranged in a shape that is identical to a rough shape of a target plant body.

2. The method as set forth in claim 1, wherein:
the plant cells having differentiation ability are dedifferentiated cells obtained from a callus.

3. The method as set forth in claim 1, wherein:
the three-dimensional body is formed from (a) the gel beads containing the plant cells having differentiation ability and (b) gel beads containing no plant cell having differentiation ability.

4. The method as set forth in claim 1, wherein:
the plant cells having differentiation ability are plant cells derived from two or more species of plants.

5. The method as set forth in claim 1, wherein:
in the step of adding the organization-promoting agent, the organization-promoting agent includes different kinds of organization-promoting agents, and the different kinds of organization promoting agents are added respectively to two or more parts of the three-dimensional body.

6. The method as set forth in claim 1, wherein:
in the step of culturing the three-dimensional body, the three-dimensional body is cultured so as to be joined to another plant body.

7. The method as set forth in claim 1, wherein:
in the step of culturing the three-dimensional body, a length direction of a part of the three-dimensional body which part corresponds to a stem is kept parallel to a gravitational direction.

8. The method as set forth in claim 1, wherein:
in the step of forming the three-dimensional body, the three-dimensional body is formed by a dipping method, an ink jet method, or a dispenser method.

9. The method as set forth in claim 1, wherein:
in the step of adding the organization-promoting agent, the organization-promoting agent is added to the three-dimensional body or the plant cells having differentiation ability, by a dipping method, an ink jet method, or a dispenser method.

10. The method as set forth in claim 9, wherein:
the organization-promoting agent is added to the three-dimensional body, by a method capable of carrying out gradation control.

11. The method as set forth in claim 1, wherein:
the three-dimensional body is subjected to arrangement control of at least leaves or stems.

\* \* \* \* \*